United States Patent
Schwellenbach et al.

(10) Patent No.: US 12,092,621 B2
(45) Date of Patent: Sep. 17, 2024

(54) METHOD OF DETERMINING THE CONCENTRATION OF AT LEAST ONE COMPOUND IN A CHROMATOGRAPHY DEVICE

(71) Applicant: Sartorius Stedim Biotech GmbH, Göttingen (DE)

(72) Inventors: Jan Schwellenbach, Göttingen (DE); Volkmar Thom, Göttingen (DE); Dominik Stein, Göttingen (DE)

(73) Assignee: Sartorius Stedim Biotech GmbH, Gottingen (DE)

( * ) Notice: Subject to any disclaimer, the term of this patent is extended or adjusted under 35 U.S.C. 154(b) by 324 days.

(21) Appl. No.: 17/595,492

(22) PCT Filed: May 8, 2020

(86) PCT No.: PCT/EP2020/062841
§ 371 (c)(1),
(2) Date: Nov. 17, 2021

(87) PCT Pub. No.: WO2020/239389
PCT Pub. Date: Dec. 3, 2020

(65) Prior Publication Data
US 2022/0214318 A1 Jul. 7, 2022

(30) Foreign Application Priority Data
May 24, 2019 (EP) .................... 19176467

(51) Int. Cl.
*G01N 30/86* (2006.01)
*G01N 30/88* (2006.01)
(Continued)

(52) U.S. Cl.
CPC ......... *G01N 30/8658* (2013.01); *G01N 30/88* (2013.01); *G16B 40/10* (2019.02);
(Continued)

(58) Field of Classification Search
None
See application file for complete search history.

(56) References Cited

U.S. PATENT DOCUMENTS 5,039,409 A * 8/1991 Blaffert ............... G01N 30/88
  210/198.2
5,582,736 A * 12/1996 Hotier ............... B01D 15/1828
  210/659
(Continued)

FOREIGN PATENT DOCUMENTS

CN 102271775 A 12/2011
CN 102323360 A 1/2012
(Continued)

OTHER PUBLICATIONS

Gritti et al, "Application of the General Height Equivalent to a Theoretical Plate Equation to Size Exclusion Chromatography," Study of the Mass Transfer of High-Molecular-Mass Compounds in Liquid Chromatography, Fabrice Anal. Chem. 2007, 79, 3188-3198.
(Continued)

*Primary Examiner* — Brandi N Hopkins
*Assistant Examiner* — Nigel H Plumb
(74) *Attorney, Agent, or Firm* — Klarquist Sparkman, LLP

(57) ABSTRACT

The present invention relates to a method of determining the concentration of at least one compound in a chromatography method, wherein fluctuations of the stationary phase's spatial structure due to variations of the composition of the mobile phase and/or the chromatography temperature are considered by calculating the concentration $c(z, t)$ based on the flow velocity $v$ and the bulk porosity $\varepsilon_b$, which may vary due to the varying composition and/or temperature and
(Continued)

which are determined for the varying composition of the mobile phase and/or the varying chromatography temperature.

15 Claims, 11 Drawing Sheets

(51) Int. Cl.
    *G16B 40/10*     (2019.01)
    *C07K 1/16*     (2006.01)
    *G01N 30/02*     (2006.01)

(52) U.S. Cl.
    CPC .......... *C07K 1/16* (2013.01); *G01N 2030/027* (2013.01); *G01N 2030/8831* (2013.01)

(56) References Cited

U.S. PATENT DOCUMENTS

| | | | | |
|---|---|---|---|---|
| 6,737,376 | B1* | 5/2004 | Heckmann | C04B 38/0045 501/12 |
| 9,766,217 | B2* | 9/2017 | Kidal | G01N 30/8693 |
| 2002/0010566 | A1* | 1/2002 | Chester | G01N 30/8693 703/2 |
| 2010/0004907 | A1* | 1/2010 | Kidal | G01N 30/8693 703/2 |

FOREIGN PATENT DOCUMENTS

| | | |
|---|---|---|
| CN | 103182198 A | 7/2013 |
| CN | 105518454 A | 4/2016 |
| CN | 106596761 A | 4/2017 |
| CN | 106596815 A | 4/2017 |
| CN | 107110835 A | 8/2017 |
| CN | 109092276 A | 12/2018 |
| EP | 0 359 320 A2 | 3/1990 |
| WO | WO9832790 A1 | 7/1998 |
| WO | WO2005121776 A1 | 12/2005 |
| WO | WO 2008/028974 A1 | 3/2008 |
| WO | WO2014030537 A1 | 2/2014 |

OTHER PUBLICATIONS

Ahmad et al., "Numerical determination of the adsorption isotherms of tryptophan at different temperatures and mobile phase compositions," *Journal of Chromatography A* 1142(2): 148-163, Feb. 2007.
Berridge, "Chemometrics and method development in high-performance liquid chromatography part 1: Introduction," *Chemometrics and Intelligent Laboratory Systems* 3(3): 175-188, Mar. 1988.
Field et al., "High-throughput investigation of single and binary protein adsorption isotherms in anion exchange chromatography employing multivariate analysis," *Journal of Chromatography A* 1510: 13-24, Jun. 2017.
Gritti et al., "Effect of the mobile phase composition on the isotherm parameters and the high concentration band profiles in reversed-phase liquid chromatography," *Journal of Chromatography A* 995(1-2): 37-54, May 2003.
Grom et al., "Protein A affinity chromatography of Chinese hamster ovary (CHO) cell culture broths containing biopharmaceutical monoclonal antibody (mAb): Experiments and mechanistic transport, binding and equilibrium modeling," *Journal of Chromatography B* 1083: 44-56, Mar. 2018.
Hupe et al., "Selection of optimal conditions in preparative liquid chromatography: I. Theory," *Journal of Chromatography A* 203: 41-52, Jan. 1981.
International Search Report and Written Opinion, dated Aug. 3, 2020, issued for International Patent Application No. PCT/EP2020/062841, 17 pages.
Mao et al., "Optimization of affinity and ion-exchange chromatographic processes for the purification of proteins," *Biotechnology and Bioengineering* 52(2): 204-222, Jun. 2014.
Piatkowski et al., "Adsorbed solution model for prediction of normal-phase chromatography process with varying composition of the mobile phase," *Journal of Chromatography A* 1092(1): 65-75, Oct. 2005.
Schwellenbach et al., "Purification of monoclonal antibodies using a fiber based cation-exchange stationary phase: parameter determination and modeling." *Bioengineering* 3(4): Dec. 24, 2016.
Vizhemehr et al., "Modeling of gas-phase filter model for high-and low-challenge gas concentrations," *Building and Environment* 80: 192-203, Jun. 2014.

* cited by examiner

- ▲ : binding components
- ◯ : stationary phase
- $c_{Feed}$ : concentration feed solution
- $c_l$ : concentration in liquid after saturation of stationary phase
- $c_{Wash}$: concentration in liquid unbound components in wash
- $c_{Elu}$ : concentration in liquid under elution conditions
- $q_{MA}$ : binding capacity stationary phase
- t : residence time ● 0.01 mol/L NaCl    ◆ 0.11 mol/L NaCl    ■ 0.21 mol/L NaCl Figure 15
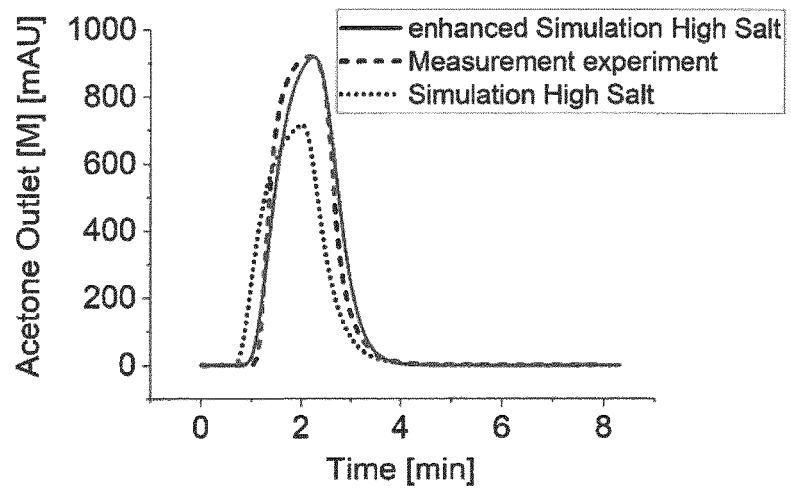
Figure 16
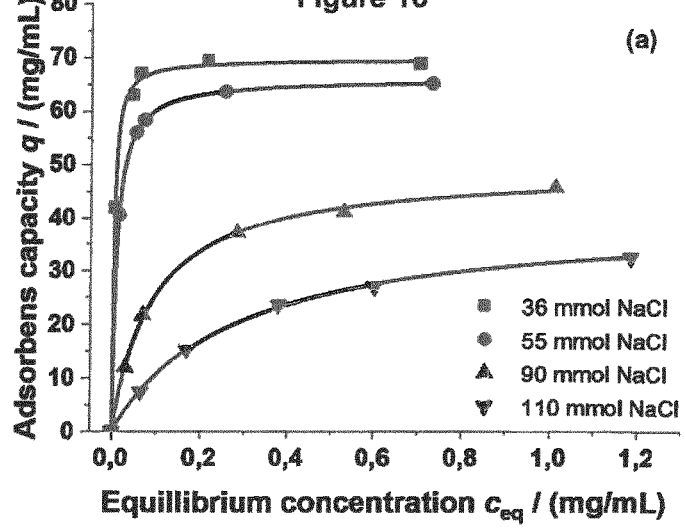
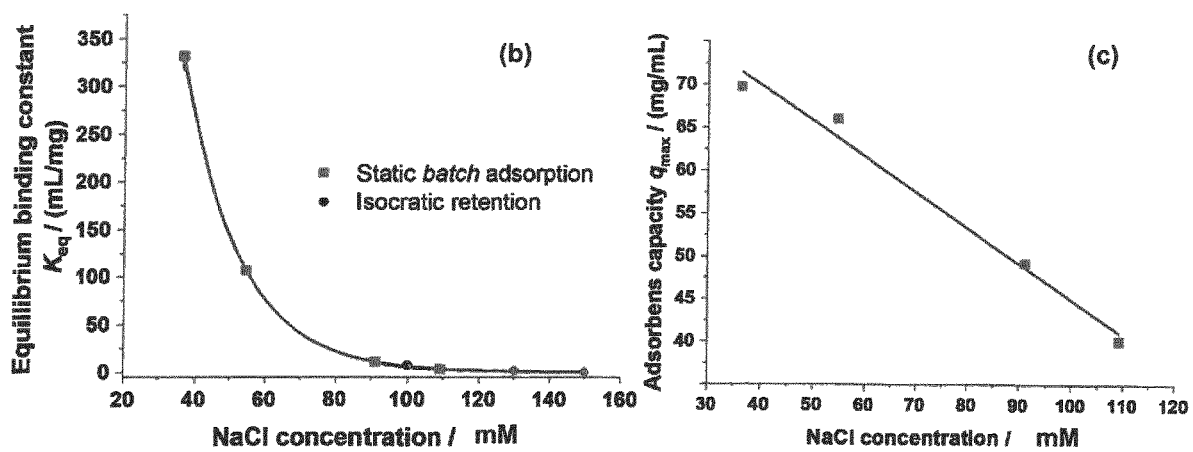

Figure 19

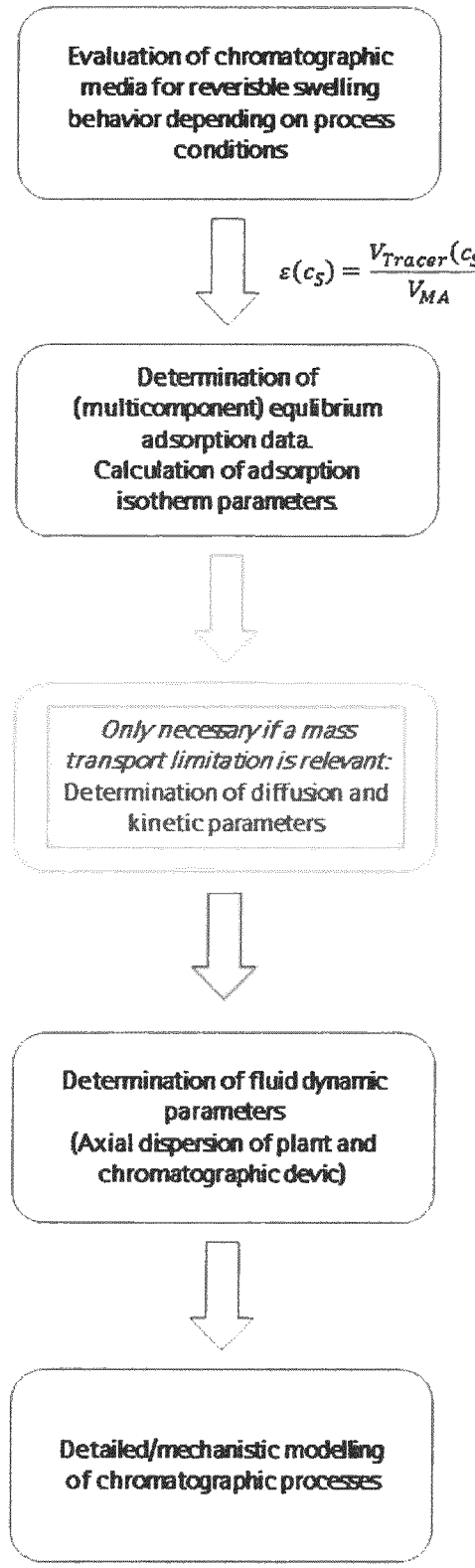

Evaluation of chromatographic media for reverisble swelling behavior depending on process conditions

Methods
- Inverse size exclusion chromatography
  - Varying process conditions ($c_S$, pH, ...)
  - Varying tracer molecule size $$\varepsilon(c_S) = \frac{V_{Tracer}(c_S)}{V_{MA}}$$

Determination of (multicomponent) equilibrium adsorption data. Calculation of adsorption isotherm parameters

Methods
- Batch experiments
- Dynamic experiments
- Isotherm parameter calculation (fitting procedure of adsorption data)
- *Use vendor provided data (chromatographic medium)*

*Only necessary if a mass transport limitation is relevant:* Determination of diffusion and kinetic parameters

Methods
- Tracer signal evaluation
- Bind&Elute gradient experiments evaluation
- Batch uptake experiments
- Mathematical calculations
- Literature known correlations

Determination of fluid dynamic parameters (Axial dispersion of plant and chromatographic devic)

Methods
- Tracer signal evaluation
- Bodenstein number
- HETP correlations
- *Use vendor provided data (chromatographic device)*

Detailed/mechanistic modelling of chromatographic processes

Targets
- Process development
- Inter- and extrapolation of process parameters
- Scale-Up

METHOD OF DETERMINING THE CONCENTRATION OF AT LEAST ONE COMPOUND IN A CHROMATOGRAPHY DEVICE

CROSS REFERENCE TO RELATED APPLICATIONS

This is the U.S. National Stage of International Application No. PCT/EP2020/062841, filed May 8, 2020, which was published in English under PCT Article 21(2), which in turn claims the benefit of European Patent Application No. 19 176 467.9, filed May 24, 2019. The prior applications are incorporated herein by reference in their entirety.

The present invention relates to a chromatography method, a method of determining the concentration of at least one compound in a chromatography method and a method of obtaining at least one chromatography method parameter. The chromatography is carried out based on the results obtained from either the method of determining the concentration of at least one compound or the method of obtaining at least one chromatography method parameter.

The analysis and modelling of mass-transfer mechanisms and kinetic phenomena involved during chromatographic operations is an important tool regarding scale-up purposes, quality-by-design approaches as well as process integration and optimization (Schwellenbach, Jan; Zobel, Steffen; Taft, Florian; Villain, Louis; Strube, Jochen (2016): Purification of Monoclonal Antibodies Using a Fiber Based Cation-Exchange Stationary Phase: Parameter Determination and Modeling. In Bioengineering (Basel, Switzerland) 3 (4). DOI: 10.3390/bioengineering3040024). Numerous mathematical models have been proposed to describe concentration profiles obtained during chromatographic operations, characterized by different complexity levels in the description of the relevant mass-transport phenomena.

Conventional models postulate that the spatial structure of the stationary phase remains constant during the chromatography process. However, under certain conditions, such as a varying composition of the mobile phase or a varying chromatography temperature, the volume of the stationary phase may vary considerably, leading to a fluctuating porosity. Therefore, conventional methods that do not take these fluctuations into account may give inaccurate results.

Specifically, many chromatographic media show a reversible swelling depending on the surrounding conditions. A prominent example are ion-exchange membrane adsorbers or porous resins bearing a grafted charged hydrogel layer (Sartobind®, Fractogel® EMD). Depending on the salt concentration, the hydrogel layer can be fully expanded due to repulsive inter- and intrachain interactions at low salt concentrations or collapsed at high salt concentrations due to shielding effects (see FIG. 1). When modelling a chromatography method without taking such kind of behavior into account, as in conventional modelling approaches, inaccurate results may be obtained.

In view of the above, the technical problem underlying the present invention is to provide a method of determining the concentration of a compound in a chromatography method that should yield accurate results despite variations of the spatial structure of the stationary phase during the chromatography; to provide a method for obtaining chromatography method parameters using the aforementioned method of determining the concentration; and a chromatography method employing the method of determining the concentration or the method for obtaining chromatography method parameters.

The solution to the above technical problem is achieved by providing the subject matter characterized in the claims.

In a first aspect, the present invention relates to a method of determining the concentration of at least one compound in a chromatography method comprising the steps of (ia) selecting the at least one compound; (ib) selecting a stationary phase; (ic) selecting a mobile phase; (id) selecting a chromatography device having a chromatography bed comprising the stationary phase and the mobile phase; (ie) selecting a chromatography temperature; wherein at least one of the composition of the mobile phase and the chromatography temperature vary; (iia) obtaining an adsorption isotherm of the at least one compound on the stationary phase for the varying composition of the mobile phase and/or the varying chromatography temperature; (iib) determining at least the flow velocity of the mobile phase in the chromatography bed $v$ and the bulk porosity of the chromatography bed $\varepsilon_b$ for the varying composition of the mobile phase and/or the varying chromatography temperature; (iii) calculating a concentration $c(z, t)$ of the at least one compound in the mobile phase at a predetermined location $z$ of the chromatography device and at a predetermined time $t$ based on the adsorption isotherm, the flow velocity $v$ and the bulk porosity $\varepsilon_b$.

According to the present invention, fluctuations of the stationary phase's spatial structure due to variations of the composition of the mobile phase and/or the chromatography temperature are considered by (iii) calculating the concentration $c(z, t)$ based on the flow velocity $v$ and the bulk porosity $\varepsilon_b$ which may vary due to the varying composition and/or temperature and which are determined for the varying composition of the mobile phase and/or the varying chromatography temperature in step (iib). Thereby, it is possible to accurately calculate the concentration $c(z, t)$ despite variations of the spatial structure of the stationary phase.

Chromatography is a physical method of separation in which the components to be separated are distributed between two phases, one of which is stationary (stationary phase) while the other one (the mobile phase) moves in a predetermined direction.

The method of the present invention is not limited to a specific type of chromatography. For instance, the inventive method can be used for adsorption chromatography, affinity chromatography, column chromatography, displacement chromatography, elution chromatography, exclusion chromatography, frontal chromatography, gas chromatography, ion-exchange chromatography, isothermal chromatography, gel-permeation chromatography, liquid chromatography, normal-phase chromatography, partition chromatography, planar chromatography, programmed-flow chromatography, hydrophobic interaction chromatography, mixed-mode chromatography, programmed-pressure chromatography, programmed-temperature chromatography, pyrolysis-gas chromatography, reaction chromatography, reversed-phase chromatography, supercritical fluid chromatography, two-dimensional chromatography and the like. The method according to the present invention is particularly suited for ion-exchange chromatography, hydrophobic interaction chromatography, affinity chromatography and mixed-mode chromatography.

In the method according to the present invention, it is possible to determine the concentration or concentrations of one or more compounds depending on the time $t$ during the process and the location $z$ of the chromatography device/the chromatography bed. In this context, the location $z$ of the chromatography device is along the above-mentioned predetermined direction in which the mobile phase moves during the chromatography. In the context of the present invention, it can be assumed that the concentration of the at least one compound does not vary in the two other directions x and y perpendicular to the direction z.

The at least one compound selected in step (ia) is not particularly limited. For instance, it can be selected among small molecules (Mn≤8000 g/mol, determined by GPC based on polystyrene standards), drugs, proteins, nucleotides, nucleosides, biological cells, viruses, virus-like particles, antibody-drug conjugates, charge variance antibodies, antibody fragments, polyaminoacids and polypeptides. Preferably, the at least one compound comprises or is a protein and/or a drug.

The method of the present invention enables the calculation of the concentration of at least one compound in a chromatography process. It is in principle possible to determine the concentration of any compound present in the mobile phase at any predetermined location z of the chromatography device and at any time t during the chromatography. Preferably, the concentration of the at least one compound is calculated at the outlet of the chromatography device for a plurality of points in time.

It is possible that the concentration of only one compound is calculated. However, it is preferable that the concentrations of two or more compounds are calculated. It is particularly preferred to calculate the respective concentration of at least two different compounds, wherein at least one compound is a target compound and the one or more further compounds are impurity compounds. Thus, it is for instance possible to determine by the method of the present invention whether the chromatography parameters selected in steps (ia) to (ie) enable a satisfactory separation of the one or more target compound(s) from the one or more impurity compound(s).

According to the present invention, a satisfactory separation between a target compound and an impurity compound means that at all times t during the chromatography only one of the target compound and the impurity compound has a significant concentration in the mobile phase at the outlet of the chromatography device. That is, the target compound and the impurity compound leave the chromatography device essentially at different times t. A significant concentration is a concentration of at least 0.01 μmol/L, preferably at least 0.001 μmol/L, particularly preferably at least 0.0001 μmol/L.

According to the present invention, step (ib) is not particularly limited. In principle, any stationary phase that is suitable for chromatography can be used. Suitable stationary phases are, for instance, porous and non-porous spherical particles, porous and non-porous non-spherical particles, for example silica particles, chromatography resins, chromatography membranes, chromatography monoliths, membrane adsorbers, wovens, non-wovens and mixed matrices. According to the present invention, an ion-exchange chromatography membrane, a hydrophobic interaction membrane, an affinity membrane or a monolith bearing the same interaction modi as the ion-exchange chromatography membrane, hydrophobic interaction membrane and/or affinity membrane is preferably selected in step (ib).

According to a preferred embodiment of the present invention, the stationary phase is reversibly swellable. A stationary phase is considered as "swellable" if a change of the composition of a mobile phase in contact with the stationary phase results in a change of the volume of the stationary phase. When the volume of the stationary phase changes, the porosity changes as well. Thus, according to the present invention, a stationary phase is considered as "swellable" if a change of the composition of a mobile phase in contact with the stationary phase results in a change of the internal porosity $\varepsilon_p$, the stationary phase porosity $\varepsilon_{sp}$ or the bulk porosity $\varepsilon_b$.

For instance, the change of the internal porosity $\varepsilon_p$, the stationary phase porosity $\varepsilon_{sp}$ or the bulk porosity $\varepsilon_b$ can be at least 5%, preferably at least 10%, particularly preferably at least 15%. The change of the respective porosity is calculated based on the ratio of the larger porosity to the smaller porosity. A stationary phase is considered as "reversibly swellable" if the change of the porosity is reversible, i.e. if the original porosity before the change of the composition of the mobile phase in contact with the stationary phase can be restored by restoring the original composition of the mobile phase.

According to a preferred embodiment of the present invention, a gel, preferably a hydrogel, is formed on at least a part of the surface of the stationary phase when the mobile phase is contacted with the stationary phase. Here, a "gel" is considered as a non-fluid network that is expanded throughout its whole volume by the mobile phase. Preferably, the gel is formed on the entire surface of the stationary phase. A "hydrogel" is a gel expanded by a mobile phase that is an aqueous medium.

According to a preferred embodiment of the present invention, at least a part of the surface of the stationary phase is constituted by a polymer that is bound to the surface of a stationary phase support structure. The stationary phase support structure is not particularly limited and may have the form of a particle, bead or a porous membrane. Preferably, the entirety of the surface of the stationary phase is constituted by the polymer. According to a particularly preferred embodiment of the present invention, a gel is formed from the polymer when it comes into contact with the mobile phase, as described above. It is even more preferred that this gel is a hydrogel.

According to the present invention, it is preferred that the chromatographic bed has an internal porosity $s_p$ of at most 0.90, preferably at most 0.5, particularly preferably at most 0.20, even more preferably at most 0.05, most preferably 0.01, for example 0.00. Moreover, it is preferred that the stationary phase has a bulk porosity $\varepsilon_b$ of from 10 to 99, preferably of from 30 to 90, even more preferably from 45 to 80. The total porosity $\varepsilon_T$ is preferably 10 to 99, more preferably 30 to 90, particularly preferably 45 to 80.

Speaking in terms of the stationary phase being constituted by a porous particulate material, the total porosity $\varepsilon_T$ of the chromatography bed can be divided into two terms:

Internal porosity/voidage $\varepsilon_p$: This term describes the internal voidage of the porous particles with respect to the total volume of the chromatography bed.

Bulk porosity/voidage $\varepsilon_b$: This term describes the voidage between the particles in the chromatography bed (flow channels) with respect to the total volume of the chromatography bed.

Both porosity values $\varepsilon_p$ and $\varepsilon_b$ can be added to yield the total porosity $\varepsilon_T$ of the chromatographic bed:

$$\varepsilon_T = \varepsilon_p + \varepsilon_b$$

The chromatography bed can be further characterized by the

Stationary phase porosity $\varepsilon_{sp}$: This term describes the internal voidage of a porous particle with respect to the total volume of the stationary phase.

$$\varepsilon_{sp} = \frac{\varepsilon_T - \varepsilon_b}{1 - \varepsilon_b} = \frac{\varepsilon_p}{1 - \varepsilon_b}$$

Not only stationary phases constituted by particulate materials can be described by the above parameters $\varepsilon_T$, $\varepsilon_p$, $\varepsilon_b$ and $\varepsilon_{sp}$ but also stationary phases in general, such as membranes, monoliths, non-wovens, wovens and other non-particular media. Depending on the structure of the stationary phase (matrix), the internal porosity $\varepsilon_p$ can equal zero, which leads to possible simplifications of the mass transport phenomena due to the absence of intra-matrix structure diffusion.

The values of the internal porosity $\varepsilon_p$, the stationary phase porosity $\varepsilon_{sp}$, the bulk porosity $\varepsilon_b$, and the total porosity $\varepsilon_T$ can be determined as explained in the following.

Inverse size exclusion chromatography (iSEC) is a widely used method to determine the voidage and porosity of chromatographic media in respect of the molecule size. A reference molecule (tracer molecule) for the inverse size exclusion chromatography has to be chosen. The size of the reference molecule should match the size of the at least one compound (e.g. a target molecule). It is preferred that the reference molecule does not interact with the stationary phase. Preferred molecule classes for the reference molecule, having a narrow and defined size distribution, are in particular but not limited to polysaccharides, polyacrylates, polystyrenes, polymethacrylates, polyacrylamides, latex beads. (Inverse size exclusion chromatography can additionally be used to calculate the pore size distribution using various models.)

A major analytical approach is represented by the conventional method of statistical moments. Applied to the chromatographic peaks resulting from a narrow rectangular pulse injection of the tracer into the system, this method is an effective approach to calculate the actual volume, voidage (porosity) and dispersion coefficient $D_{ax}$ of the chromatography bed.

Following the moment analysis technique, a voidage value, depending on buffer conditions and molecule size, can be calculated using the following approach:

$$\varepsilon = \frac{V}{F/\mu_p} \quad (1)$$

where $\varepsilon$ represents the volume fraction accessible for the tracer molecule (reference molecule), V the chromatography bed volume, F the volumetric flow rate and $\mu_p$ the first moment of a tracer peak.

For all signals, the first ($\mu_p$) and second ($\sigma_p^2$) moments can be measured and calculated as proposed by H. W. Haynes (A Model for the Application of Gas Chromatography to measurements of Diffusion in Bidisperse Structured Catalysts, AIChE J. 19 (1973) 1043-1046. doi:10.1002/aic.690190526) and corrected, if necessary, by subtracting the moments attributed to the extra-column volume of the chromatography device (such as a HPLC system).

This correction procedure can be performed by determining the first ($\mu_{HPLC}$) and second ($\sigma_{HPLC}^2$) moment of a tracer signal measured in the absence of the chromatographic medium. The respective value is then subtracted from the first ($\mu_{p,obs}$) and second ($\sigma_{p,obs}^2$) moment determined in the presence of the chromatographic medium to eliminate the influence of the chromatographic system (see the below formulae (4) and (5)).

$$\mu_{p,obs} = \frac{\int_0^\infty C_{d,i}(t) \cdot t \cdot dt}{\int_0^\infty C_{d,i}(t) \cdot dt} \quad (2)$$

$$\sigma_{p,obs}^2 = \frac{\int_0^\infty C_{d,i}(t) \cdot (t - \mu_{p,obs})^2 \cdot dt}{\int_0^\infty C_{d,i}(t) \cdot dt} \quad (3)$$

$$\mu_p = \mu_{p,obs} - \mu_{HPLC} \quad (4)$$

$$\sigma_p^2 = \sigma_{p,obs}^2 - \sigma_{HPLC}^2 \quad (5)$$

where $\mu_p$ and $\sigma_p^2$ are the first and second moment of the tracer peak. $\mu_{p,obs}$ and $\sigma_{p,obs}^2$ are attributed to the whole system, whereas $\mu_{HPLC}$ and $\sigma_{HPLC}^2$ correspond only to the extra column volume. $C_{d,i}(t)$ represents the concentration of the tracer r at a detector at time t. That is, the concentration $C_{d,i}(t)$ is detected by the detector.

If the chromatography bed has no internal porosity, the bulk porosity $\varepsilon_b$ can be directly obtained with respect to the used molecule size by applying formulae (1), (2) and (4). In this case, $\varepsilon_b = \varepsilon = \varepsilon_T$, $\varepsilon_p = 0$ and $\varepsilon_{sp} = 0$.

If the chromatography bed has an internal porosity $\varepsilon_p$ and a stationary phase porosity $\varepsilon_{sp}$, the values of $\varepsilon_p$ and $\varepsilon_{sp}$ can be determined using the following approach:

Small tracer molecules can completely access the internal voidage $\varepsilon_p$, reflecting the stagnant phase, as well as the volume $\varepsilon_b$ in the larger transport channels, occupied by the mobile phase. The obtained boundary value for the accessible volume fraction reflects therefore the total voidage $\varepsilon_T$ of the chromatography bed. That is, in case a small molecule such as acetone is used as a tracer i, $\varepsilon = \varepsilon_T$ in formula (1).

Large tracer molecules i are completely excluded from the internal voidage $\varepsilon_p$. The obtained boundary values for the accessible volume fraction reflects the external voidage (bulk porosity) $\varepsilon_b$, which is occupied by the mobile phase. That is, in case a large molecule such as dextran having a weight-average molecular weight $M_w$ determined by size exclusion chromatography of 2 000 000 g/mol is used as a tracer i, $\varepsilon = \varepsilon_b$ in formula (1). Both boundary values are necessary to describe the stationary phase porosity of the chromatography bed $\varepsilon_{sp}$:

$$\varepsilon_{sp} = \frac{\varepsilon_T - \varepsilon_b}{1 - \varepsilon_b}$$

The same approach can be used for the internal porosity $\varepsilon_p$. Both values for the external and the total porosity are necessary for its calculation ($\varepsilon_p = \varepsilon_T - \varepsilon_b$).

The determination of $\varepsilon_p$ and $\varepsilon_{sp}$ needs therefore one tracer molecule with no accessibility to the internal porosity (such as dextran) and another tracer molecule with complete accessibility to the internal porosity (such as acetone). A combination of formulae (1), (2) and (4) makes it possible to calculate the value of $\varepsilon_p$ or $\varepsilon_{sp}$ as described in detail in J. Schwellenbach, S. Zobel, F. Taft, L. Villain, J. Strube, Purification of monoclonal antibodies using a fiber based cation-exchange stationary phase: parameter determination and modeling, Bioengineering 3 (2016) 24/1-24/20. doi: 10.3390/bioengineering3040024.

In case it is unknown whether the internal porosity $\varepsilon_p$ of the chromatographic bed is zero or not, the stationary phase is dealt with in accordance with the above method for determining the internal porosity $\varepsilon_p$. If $\varepsilon_p$ is zero, the experiments with the small and large tracer molecules will yield the same result for E in formula (1), i.e. $\varepsilon_b = \varepsilon_T$, and the resulting value for $\varepsilon_p$ according to the formula "$\varepsilon_p = \varepsilon_T - \varepsilon_b$" will be 0.

In case the stationary phase is constituted by a particulate material such as silica particles, the internal porosity $\varepsilon_p$ of the chromatographic bed reflects the porosity within the particles. Contrary thereto, the bulk porosity $\varepsilon_b$ is constituted by the space between the particles without taking the internal porosity $\varepsilon_p$ into account. The total volume accessible by the mobile phase (total porosity $\varepsilon_T$) is the sum of the bulk and internal porosities ($\varepsilon_T = \varepsilon_p + \varepsilon_b$).

The determination of these voidage values $\varepsilon_p$, $\varepsilon_{sp}$, $\varepsilon_b$, and $\varepsilon_T$ can be carried out for different compositions of the mobile phase and at different temperatures. For instance, different conditions with respect to salt concentration, pH and temperature can be used to determine a functional relation, as described in detail in the context of step (iib) of the inventive method.

According to the present invention, any mobile phase that can be used in a chromatography method can be selected in step (ic). The mobile phase is preferably liquid. Moreover, the mobile phase can include or be an organic solvent or a mixture of organic solvents. In addition to one or more organic solvents, the mobile phase can include water. Preferably, the mobile phase is an aqueous medium. The composition of the mobile phase can vary during the chromatography method (gradient chromatography). For instance, when the mobile phase includes one or more organic solvents, the concentration of the one or more organic solvents may be changed during the chromatography. Moreover, when the mobile phase is an aqueous medium, the pH and/or the salt concentration of the mobile phase can vary during the chromatography method.

According to the present invention, the pH of the mobile phase can in principle take any value. Preferably, the pH has a value of from 0 to 14, more preferably 2 to 12, particularly preferably 3 to 11, even more preferably 4 to 10, and most preferably 5 to 9. Of course, the pH may also be kept constant during the chromatography method.

According to the present invention, the salt concentration of the mobile phase can in principle take any value, as long as the solubility of the salt(s) in the mobile phase is not exceeded. Preferably, the salt concentration has a value ranging from 0 to 10 mol/L, more preferably 0 to 5 mol/L, particularly preferably between 0 to 3 mol/L, most preferably 0 to 1 mol/L. Of course, the salt concentration may also be kept constant during the chromatography method.

According to the present invention, one or more salts may be dissolved in the mobile phase, as mentioned above. The one or more salts are not particularly limited. Preferably, the one or more salts are selected from the group consisting of sodium chloride, potassium chloride, sodium sulfate, sodium carbonate, potassium sulfate, potassium dihydrogenphosphate, dipotassium hydrogenphosphate, ammonium sulfate, urea hydrochloride, guanidine hydrochloride, disodium hydrogenphosphate, sodium dihydrogenphosphate, tris(hydroxymethyl)aminomethane hydrochloride, glycine, trisodium citrate and combinations thereof. The mobile phase may alternatively or additionally contain the corresponding acids, such as hydrochloric acid, sulfuric acid, citric acid, etc.

The chromatography device selected in step (id) is not particularly limited. The chromatography device can have any size, from the laboratory scale, where the volume $V_b$ of the chromatography bed is at most 500 mL, preferably at most 100 mL, particularly preferably at most 20 mL, even more preferably at most 5 mL, to the industrial scale, where the volume $V_b$ of the chromatography bed is more than 500 mL, preferably at least 1 L, particularly preferably at least 5 L, even more preferably at least 10 L. Preferably, the volume $V_b$ is at least 0.01 mL, more preferably at least 0.1 mL, particularly preferably at least 0.5 mL. It is further preferred that the volume $V_b$ is at most 1000 L, more preferably at most 500 L. Preferably, the chromatography device has a volume $V_b$ of the chromatography bed of more than 500 mL.

Preferably, step (id) does not only include the selection of the chromatography device but also the selection of at least one tank, a liquid pump, a detector, a plurality of valves and a process control software (selection of chromatography set-up), without being limited thereto. The chromatography set-up may vary in its machinery and systems by the processing complexity. For instance, the tank can be omitted e.g. when the chromatography method is a continuous chromatography method. In the exemplary chromatographic set-up displayed in FIG. 18, the reciprocating pump P1 promotes the feed solution from the feed tank B1 to the chromatographic device, here a membrane adsorber MA1. The corresponding detector signal is detected preferably downstream of the chromatographic device MA1. Thereafter, the mobile phase is preferably collected in a tank B2 or further purified. Impurities are preferably directed to a waste collector (not displayed in FIG. 18).

In step (ie) of the inventive method, a chromatography temperature is selected. The chromatography temperature is not particularly restricted as long as it is possible to carry out the chromatography at the selected temperature. Preferably, the chromatography temperature is more than 0° C., more preferably at least 1° C., particularly preferably at least 5° C., even more preferably at least 15° C. The upper limit of the chromatography temperature is preferably less than 100° C., preferably 80° C. or less, more preferably 70° C. or less, particularly preferably 60° C. or less, even more preferably 50° C. or less. The chromatography temperature may be varied during the chromatography method, preferably within the above-specified ranges. Preferably, the chromatography temperature is constant.

In step (iia) of the inventive method, an adsorption isotherm of the at least one compound on the stationary phase is obtained for the varying composition of the mobile phase and/or the varying chromatography temperature. The adsorption isotherm is an equation that relates the binding capacity q to the concentration of the at least one compound in the mobile phase, i.e. an equation having the form $q=f(c)$. According to the present invention, the binding capacity $q(z,t)$ is understood as the proportion of the at least one compound that is adsorbed on the stationary phase instead of being located in the mobile phase and is expressed in mol/L, with respect to a certain time t and location z.

According to the present invention, the adsorption isotherm can be obtained experimentally, which is preferred. Thus, according to a preferred embodiment of the present invention, step (iia) of obtaining the adsorption isotherm involves one or more laboratory experiments. Preferably, equilibrium adsorption data are obtained by means of laboratory experiments. Specifically, batch experiments can be used, as they offer a low need for target molecule and can be automated. Other experiments based on uptake within a packed chromatography bed under dynamic conditions can also be used as the resulting equilibrium data is identical but higher amounts of target molecule are required.

A person skilled in the art is able to determine an adsorption isotherm based on his background knowledge. For instance, the adsorption isotherm obtained in step (iia)

can be a steric-mass-action (SMA) adsorption isotherm, a Langmuir adsorption isotherm or a Freundlich adsorption isotherm.

According to a preferred embodiment of the present invention, an SMA isotherm can be used as the adsorption isotherm. The SMA isotherm can be used in order to describe the adsorption of the at least one compound in dependence on influencing factors like the salt concentration and/or pH. An SMA isotherm can be determined as described in detail in Brooks, Clayton A.; Cramer, Steven M. (1992): Steric mass-action ion exchange. Displacement profiles and induced salt gradients. In AIChE J. 38 (12), pp. 1969-1978. DOI: 10.1002/aic.690381212; and in Journal of Chromatography A, 1233 (2012) 54-65 "Determination of parameters for the steric mass action model—A comparison between two approaches". The SMA isotherm is preferred when the stationary phase is an ion-exchange chromatography membrane.

In the following three equations, the electro neutrality in dependency of the steric factor $\sigma_i$ of the at least one compound, characteristic charge $v_1$ of the at least one compound and binding capacity of counter ions $q_1$ ($q_1$ is the binding capacity of the salt) as well as the binding capacity $q_j$ of the at least one compound are shown. In the formulae, n is the number of the at least one compounds and $\Lambda$ is the ionic capacity of the chromatographic medium (stationary phase).

$$\Lambda = q_1 + \sum_{i=2}^{n+1}(v_i + \sigma_i)q_i$$

$$\Lambda = q_1 + \sum_{i=2}^{n+1} v_i \cdot q_i$$

$$q_i = q_1 - \sum_{i=2}^{n+1} \sigma_i \cdot q_i$$

The ionic capacity $\Lambda$ of the chromatographic medium defines the number of ligands on the chromatographic backbone. The ionic capacity (or capacity of a chromatographic medium) $\Lambda$ can be determined by means of a chemical reaction of the ligands on the backbone with a characteristic component which binds to each of the ligands or by means of titration. For ion exchange chromatography (IEX), the ionic capacity $\Lambda$ is determined by titration of the charged ligands by the corresponding acid or base.

For a rapid equilibrium or in equilibrium state, the SMA isotherm can be written as in the following equation.

$$c_i = \frac{q_i}{k} \cdot \left(\frac{c_1}{\Lambda - \sum_{i=2}^{n+1}(v_i + \sigma_i)q_i}\right)^{v_i}$$

In the above equation, $c_i$ is the concentration of the at least one compound and $c_1$ is the salt concentration at the binding site.

The characteristic charge $v_i$ and the equilibrium constant k can be determined by the curve evaluation of the capacity factor log k' with the equation $$k' = \frac{1-\varepsilon_T}{\varepsilon_T} \cdot \left(\frac{q_i}{c_i}\right)$$

in the equation $$\log k' = \log\left(\frac{1-\varepsilon_T}{\varepsilon_T} \cdot k \cdot \Lambda^{v_i}\right) - v_i \cdot \log(c_1).$$

Using a linear regression of logarithmic capacity factor over logarithmic salt concentration results in the charge $v_i$ and equilibrium constant k by slope and intercept. The steric factor $\sigma_i$ can be fitted by error minimization on the experimental results or calculated with the following equations for $c_i \rightarrow \infty$; $q_1 \rightarrow 0$;

$$\lim_{c_i \rightarrow \infty} q_i = q_i^{max} = \frac{\Lambda}{\sigma_i + v_i}$$

According to another preferred embodiment of the present invention, a Langmuir isotherm can be obtained in step (iia).

A Langmuir isotherm can be written for multiple components (i.e. in case there the number of the at least one compound is 2 or more) in the following form $$q_i = \frac{K_{eq,i} \cdot q_{max,i} \cdot c_i}{1 + \sum_{j=1}^{n} K_{eq,j} \cdot c_j}$$

where $q_i$ represents the binding capacity for compound i, $K_{eq,i}$ is the equilibrium adsorption constant, $q_{max,i}$ is the maximum binding capacity of the chromatographic medium and $c_i$ is the concentration of compound i in the mobile phase. Moreover, the sum $\Sigma_{j=1}^{n} K_{eq,j} \cdot c_j$ includes all components present in the mobile phase that are able to adsorb to the stationary phase, including compound i.

Following the work published by Yamamoto et al. (Biotechnology and Bioengineering, Vol XXV, Pp. 1465-1583 (1983)) and Forrer (Nicola Forrer, "Antibody purification with ion-exchange chromatography", dissertation, ETH Zurich 2008), the Langmuir parameters, namely the maximum binding capacity $q_{max,i}$ and the equilibrium binding constant $K_{eq,i}$, can be related to the salt concentration or pH within the fluid phase to describe the salt/pH dependent binding behavior. In the following equations, the salt concentration or the pH are expressed by $c_{mod}$.

$$q_{max,i} = a_1 \cdot c_{mod} + a_2$$

$$K_{eq,i} = b_1 \cdot \exp(-b_2 \cdot c_{mod})$$

The parameters $a_1$, $a_2$, $b_1$ and $b_2$ are coefficients used to describe the salt dependency of the isotherm parameters $K_{eq,i}$ and $q_{max,i}$. If the isotherm parameters have been acquired for different salt concentrations, the coefficients can be determined by a least-square fit of the above shown functions to the salt dependent isotherm parameter data sets.

In case one or more of the conditions selected from the group consisting of the chromatography temperature, the pH of the mobile phase and the salt concentration of the mobile phase varies, several adsorption isotherms need to be obtained for each of the varying condition(s) in step (iia) so as to cover the whole range of chromatography temperatures, the whole range of the pH of the mobile phase and/or the whole range of the salt concentration of the mobile phase. In such a case, the adsorption isotherms for only some of the varying conditions can be obtained according to the present invention, while the adsorption isotherms for the other conditions can be obtained by means of interpolation using a functional relation, which describes the obtained data sets. A similar approach as described for the salt-dependency of the isotherm parameters can be used for the temperature or pH dependency.

In step (iib) of the inventive method, at least the flow velocity of the mobile phase in the chromatography bed $v$ and the bulk porosity of the chromatography bed $\varepsilon_b$ are determined for the varying composition of the mobile phase and/or the varying chromatography temperature. Based on the adsorption isotherm as well as the parameters $v$ and $\varepsilon_b$, it is possible to perform step (iii) based on the equilibrium model described below.

The bulk porosity $\varepsilon_b$ can be determined as described above. The value of $v$ can be calculated based on the following equation $$v = \frac{F}{A \cdot \varepsilon_b}$$

where F is the volumetric flow rate of the mobile phase (which is predetermined) and A is the cross-section area of the chromatography device selected in step (id). The value of A can be determined by a straightforward geometric calculation.

According to a preferred embodiment of the present invention, in step (iib), the axial dispersion coefficient $D_{ax}$ of the at least one compound in the chromatography bed is further determined for the varying composition of the mobile phase and/or for the varying chromatography temperature and in step (iii), the calculation of the concentration c(z, t) is further based on the axial dispersion coefficient $D_{ax}$. Based on the adsorption isotherm as well as the parameters $v$, $\varepsilon_b$ and $D_{ax}$, it is possible to perform step (iii) based on the equilibrium dispersive model described below.

The axial dispersion coefficient $D_{ax}$ of the at least one compound in the chromatography bed can be calculated based on the following equation $$D_{ax} = \alpha \cdot v$$

where $\alpha$ is a dispersivity factor. This factor can be determined by measuring the axial dispersion coefficient at different linear flow velocities via a linear regression as shown in Example 5. In a similar manner, the axial dispersion coefficient $D_{ax,DPF}$ of the at least one compound in the hypothetical DPF as described below can be calculated using the equation $D_{ax,DPF} = \alpha_{DPF} \cdot v$.

Alternatively, the axial dispersion coefficient $D_{ax}$ can be calculated from the following equation.

$$D_{ax} = \frac{vL}{Bo}$$

In the above equation, Bo is the Bodenstein number, $v$ is the linear velocity and L is a characteristical length. The Bodenstein number is determined by a pulse tracer experiment in which the axial dispersion coefficient is either fitted to the experimental data with error minimization or using the moment analysis. The characteristical length is the chromatography bed height (see Octave Levenspiel; Traxer Technology Modeling of the Flow of Fluids ISBN: 978-1-4419-8073-1).

As an alternative, the axial dispersion coefficient $D_{ax}$ can be calculated from the following equations.

$$D_{ax} = HETP \cdot \frac{v}{2 \cdot \varepsilon_b}$$

$$HETP = \frac{\sigma^2}{L} \frac{v}{\varepsilon_b}$$

In the above equations, HETP is the Height Equivalent to one Theoretical Plate and $v$ is as defined above. HETP can be determined by tracer experiments in which the variance $\sigma$ of the corresponding peak, at a given linear velocity $v$ and characteristic length L (chromatography bed height) is used.

Moreover, it is further preferred that in step (iib), the internal porosity $\varepsilon_p$ of the chromatography bed and/or the stationary phase porosity $\varepsilon_{sp}$ is further determined for the varying composition of the mobile phase and/or the varying chromatography temperature in addition to $v$, $\varepsilon_b$ and $D_{ax}$, and in step (iii), the calculation of the concentration c(z, t) is based on $v$, $\varepsilon_b$, $D_{ax}$ as well as $\varepsilon_p$ and/or $\varepsilon_{sp}$. Based on the adsorption isotherm as well as the parameters $v$, $\varepsilon_b$, $D_{ax}$ and $\varepsilon_p/\varepsilon_{sp}$, it is possible to perform step (iii) based on the lumped pore model or the general rate model described below.

In step (iib), the above parameters are determined for several compositions of the mobile phase (e.g. for several pH values and/or for several salt concentrations) and/or for several temperatures. Preferably, the chromatography temperature is kept constant so that only the composition of the mobile phase varies, e.g. the salt concentration and/or the pH. For each varying parameter (e.g. temperature, pH, salt concentration), at least two, preferably at least three, more preferably at least four values are determined for $v$, $\varepsilon_b$ and optionally $D_{ax}$, $\varepsilon_{sp}$, and $\varepsilon_p$. The higher this number, the higher the accuracy of the inventive method. However, for the sake of efficiency, this number should be at most 10, preferably at most 7, particularly preferably at most 6.

According to the present invention, the values of $v$, $\varepsilon_b$ and optionally $D_{ax}$, $\varepsilon_{sp}$ and $\varepsilon_p$ obtained in step (iib) can be taken directly in step (iii). In that case, ranges of the varying composition of the mobile phase and/or the varying chromatography temperature can be defined where the respective values obtained in step (iib) apply. For example, in case $v$ was determined for an NaCl concentration of 2 mM and 4 mM, i.e. $v$(2 mM) and $v$(4 mM), $v$(2 mM) could be taken as the linear velocity for NaCl concentrations of up to 3.0 mM and $v$(4 mM) could be taken as the linear velocity for NaCl concentrations of more than 3.0 mM.

According to a preferred embodiment of the present invention, the values of $v$, $\varepsilon_b$ and optionally $D_{ax}$, $\varepsilon_{sp}$ and $\varepsilon_p$ determined in step (iib) are interpolated and the value of $v$, $\varepsilon_b$ and optionally $D_{ax}$, $\varepsilon_{sp}$ and $\varepsilon_p$ as taken in step (iii) is based on the interpolation. According to the present invention, the interpolation can be carried out by defining a linear function for each two adjacent values of $v$, $\varepsilon_b$ and optionally $D_{ax}$, $\varepsilon_{sp}$ and $\varepsilon_p$, i.e., in pictorial terms, by drawing a line between each two adjacent values of $v$, $\varepsilon_b$ and optionally $D_{ax}$, $\varepsilon_{sp}$ and $\varepsilon_p$.

Preferably, the interpolation is performed by fitting to a mathematical function, for instance a least squares fit. It is further preferred that the fit has an accuracy $R^2$ of at least 0.90, particularly preferably of at least 0.95. Suitable fitting functions can be selected among a linear function, a polynomial function, a logarithmic function such as log or ln, an exponential function, a Boltzmann function, etc.

In step (iii) of the inventive method, a concentration c(z, t) of the at least one compound in the mobile phase is calculated at a predetermined location z of the chromatography device and at a predetermined time t based on the adsorption isotherm, the flow velocity v and the bulk porosity $\varepsilon_b$. As already outlined above, the calculation in step (iii) may further be based on the axial dispersion coefficient $D_{ax}$. In addition, the internal porosity $\varepsilon_p$ and/or the stationary phase porosity $\varepsilon_{sp}$ may be taken into account.

According to a preferred embodiment of the present invention, in step (iii), c(z, t) is calculated based on the following equation $$\frac{\partial c(z, t)}{\partial t} = Z$$

wherein Z is a sum including the following terms $$-\frac{(1-\varepsilon_b)}{\varepsilon_b} \cdot \frac{\partial q(z, t)}{\partial t} \text{ and}$$

$$-v\frac{\partial c(z, t)}{\partial z}$$

wherein
q(z, t) represents the binding capacity of the at least one compound by the stationary phase.

In this context, it has already been mentioned that the values of v, $\varepsilon_b$, $D_{ax}$ etc. may vary depending on the chromatography temperature and the composition of the mobile phase (salt concentration, pH). Therefore and since the chromatography temperature and the composition of the mobile phase may vary depending on the location in the stationary phase z and the time t, also the values of v, $\varepsilon_b$, $D_{ax}$ etc. may vary depending on the location in the stationary phase z and the time t, i.e. v=v(z, t), $\varepsilon_b=\varepsilon_b(z,t)$, $D_{ax}=D_{ax}(z, t)$ etc.

According to a preferred embodiment of the present invention, $$Z = -v\frac{\partial c(z, t)}{\partial z} - \frac{(1-\varepsilon_b)}{\varepsilon_b} \cdot \frac{\partial q(z, t)}{\partial t},$$

i.e. the concentration c(z, t) is calculated based on an equilibrium model.

A person skilled in the art is able to calculate c(z, t) based on the equation $$\frac{\partial c(z, t)}{\partial t} = Z$$

by relying on his background knowledge. Preferably, calculating c(z, t) based on the equation $$\frac{\partial c(z, t)}{\partial t} = Z$$

is carried out by using a computer, particularly preferably by a computer-based numerical method.

Preferably, the sum Z further includes the term $$+D_{ax}\frac{\partial^2 c(z, t)}{\partial z^2}$$

According to a preferred embodiment of the present invention, $$Z = -v\frac{\partial c(z, t)}{\partial z} + D_{ax}\frac{\partial^2 c(z, t)}{\partial z^2} - \frac{(1-\varepsilon_b)}{\varepsilon_b} \cdot \frac{\partial q(z, t)}{\partial t},$$

i.e. the concentration c(z, t) is calculated based on an equilibrium dispersive model.

According to another preferred embodiment of the present invention, the concentration c(z, t) is calculated based on a lumped pore model, according to which $$Z = -v\frac{\partial c(z, t)}{\partial z} + D_{ax}\frac{\partial^2 c(z, t)}{\partial z^2} - \frac{(1-\varepsilon_b)}{\varepsilon_b} \cdot A \cdot k_{eff} \cdot (c - c_f)$$

with the provision that $$\varepsilon_{sp}\frac{\partial c_f(z, t)}{\partial t} + (1-\varepsilon_{sp})\frac{\partial q_f(z, t)}{\partial t} = A \cdot k_{eff} \cdot (c - c_f)$$

where $k_{eff}$ is the global mass-transfer coefficient, $c_f$ is the volume average value of the solute concentration in the stationary phase, $q_f$ is the volume average value of the solute concentration bound on the stationary phase, and A is the specific exchange area of the stationary phase.

The exchange surface area A and the effective film diffusion coefficient $k_{eff}$ can be combined into a single rate coefficient $k_{eff,A}$:

$$k_{eff,A} = A \cdot k_{eff}$$

The global mass-transfer coefficient $k_{eff}$ satisfies the following equation $$\frac{1}{k_{eff}} = \frac{1}{k_{ext}} + \frac{1}{k_{int}}$$

where $k_{ext}$ is the external mass transfer coefficient and $k_{int}$ is the internal mass transfer coefficient.

According to the general rate model and the lumped pore model, it is assumed that the surface of the stationary phase is covered with a stagnant layer/phase of the composition constituting the mobile phase. It is further assumed that the mobile phase forms a layer of laminar flow in proximity to the stagnant phase. Mass transport from the mobile phase to the stationary phase takes place through the layer of laminar flow and through the stagnant layer.

The external mass-transfer coefficient $k_{ext}$ characterizes the mass transport from the mobile phase to the stagnant phase surrounding the stationary phase and can be determined by an evaluation of the Sherwood number Sh:

$$Sh = \frac{k_{ext} \cdot d_P}{D_{bulk}}$$

where $d_p$ represents a characteristic diameter for the flow of the mobile phase, e.g. the pore diameter in a membrane. It can be determined using scanning electron microscopy or liquid-liquid displacement porosimetry. The parameter $D_{bulk}$ represents the molecular diffusion coefficient of the at least one compound.

According to the present invention, the Einstein-Stokes equation can be used to estimate the bulk diffusion coefficient $D_{bulk}$ based on the molecule radius r, the dynamic viscosity of the solvent ϑ, the temperature T and the Boltzmann constant $k_B$:

$$D_{bulk} = \frac{k_B T}{6\pi \eta r}$$

Under defined conditions, the molecule radius r can be determined using dynamic light scattering. This method relies on the intensity fluctuation of scattered light caused by molecular motions in solution. This method also offers a direct access to the diffusion coefficient.

The solution viscosity η can be determined using a falling-sphere viscosimeter. Stokes' law is the basis of the falling-sphere viscometer, in which the fluid is stationary in a vertical glass tube. A sphere of known size and density is allowed to descend through the liquid. If correctly selected, it reaches terminal velocity, which can be measured by the time it takes to pass two marks on the tube. Electronic sensing can be used for opaque fluids. Knowing the terminal velocity, the size and density of the sphere, and the density of the liquid, Stokes' law can be used to calculate the viscosity of the fluid.

According to the present invention, Sh can be calculated based on the Schmidt (Sc) and Reynolds (Re) number (E. J. Wilson, C. J. Geankoplis, Liquid mass transfer at very low Reynolds numbers in packed beds, Ind. Eng. Chem. Fundam. 5 (1966) 9-14. doi:10.1021/i160017a002):

$$Sh = \frac{1,09}{\varepsilon_b} \cdot Sc^{0.33} \cdot Re^{0.33} \text{ for } 0.0015 < Re < 55$$

The Reynolds number Re is the dimensionless ratio of inertial forces to viscous forces within a fluid which is subjected to relative internal movement due to different fluid velocities, which is known as a boundary layer in the case of a bounding surface such as the interior of a pipe.

$$Re = \frac{\rho v L}{\mu} = \frac{vL}{v}$$

ρ is the density of the mobile phase (SI units: kg/m³)
v is the linear velocity of the mobile phase (m/s)
L is the height of the chromatography bed (m)
μ is the dynamic viscosity of the mobile phase (Pa·s or N·s/m² or kg/m·s)
v is the kinematic viscosity of the mobile phase (m²/s).

The Schmidt number (Sc) is a dimensionless number defined as the ratio of momentum diffusivity (kinematic viscosity) and mass diffusivity, and is used to characterize fluid flows in which there are simultaneous momentum and mass diffusion convection processes.

$$Sc = \frac{v}{D} = \frac{\mu}{\rho D}$$

where:
v is the kinematic viscosity of the mobile phase (m²/s).
D is the mass diffusivity (m²/s).

μ is the dynamic viscosity of the mobile phase (Pa·s or N·s/m² or kg/m·s)
ρ is the density of the mobile phase (SI units: kg/m³)

According to the present invention, the internal mass-transfer coefficient $k_{int}$, characterizing the "lumped" mass transport within the stagnant phase surrounding the stationary phase can be calculated as follows (E. Glueckauf, Theory of chromatography. VII. The general theory of two solutes following non-linear isotherms, Discuss. Faraday Soc. 7 (1949) 12. doi:10.1039/df9490700012):

$$k_{int} = 5 \frac{D_{eff}}{R_p}$$

where $D_{eff}$ denotes the effective molecular diffusion coefficient within the stagnant phase, which can be calculated as described in K. Kaczmarski, D. Antos, H. Sajonz, P. Sajonz, G. Guiochon, Comparative modeling of breakthrough curves of bovine serum albumin in anion-exchange chromatography, J. Chromatogr. A. 925 (2001) 1-17. doi: 10.1016/S0021-9673(01)01035-4, and $R_p$ denotes the particle radius, which can be determined using scanning electron microscopy or liquid-liquid displacement porosimetry.

The effective diffusion coefficient $D_{eff}$ is often by an order of magnitude lower in a porous system like a chromatographic resin or the hydrogel layer of a membrane adsorber due to the movement in a constricted pore system. This can be summarized as the tortuosity factor τ.

$$D_{eff} = \frac{D_{bulk}}{\tau}$$

Thus, based on the bulk diffusion coefficient $D_{bulk}$ and the tortuosity factor τ, the effective diffusion constant $D_{eff}$ can be calculated.

Following the correlation published by Mackie and Meares (J. S. Mackie, P. Meares, The Diffusion of Electrolytes in a Cation-Exchange Resin Membrane. I. Theoretical, Proc. R. Soc. London. Ser. A. Math. Phys. Sci. 232 (1955) 498-509. http://rspasoyalsocietypublishing.org/content/232/1191/498.abstract.), the tortuosity factor can be calculated using the stationary phase porosity $\varepsilon_{sp}$:

$$\tau = \frac{(2 - \varepsilon_{sp})^2}{\varepsilon_{sp}^2}$$

The stationary phase porosity $\varepsilon_{sp}$ can be determined as described above.

The parameter $k_{int}$ can be interpreted as a mass-transfer resistance caused by a flat diffusive layer with a thickness of $R_p/5$.

The above approach for calculating $k_{int}$ of stationary phases that are constituted by spherical porous particles can be transferred to stationary phases that are not constituted by spherical porous particles. Assuming that the stationary phase has a uniform distribution of adsorption sites on its surface and that the diffusive pathway a solute molecule of the at least one compound has to travel within the stagnant phase before reaching an adsorption site, can be denoted as $d_H/2$ (J. Schwellenbach, S. Zobel, F. Taft, L. Villain, J. Strube, Purification of monoclonal antibodies using a fiber based cation-exchange stationary phase: parameter determination and modeling, Bioengineering 3 (2016) 24/1-24/20. doi:10.3390/bioengineering3040024), $k_{int}$ can also be calculated based on the following equation:

$$k_{int} = 2\frac{D_{eff}}{d_h}$$

where $d_h$ denotes the thickness of the stagnant phase. In the case of a membrane adsorber, the stagnant phase can be interpreted as the hydrogel layer thickness. It can be calculated as follows:

$$d_h = \frac{(\varepsilon_{in} - \varepsilon_{ex}) \cdot V_b}{A_{spec} \cdot m}$$

where $d_h$ is the hydrogel layer thickness, $V_b$ the column volume, $A_{spec}$ the specific surface area, m the membrane adsorber mass and $\varepsilon_{in}$ and $\varepsilon_{ex}$ the porosity value obtained for a complete accessibility of the hydrogel layer, as seen for a small tracer molecule (e.g. acetone), and complete exclusion from the hydrogel layer, as observed for large tracer molecules with a hydrodynamic radius $r_H$>15 nm (e.g. dextrane having a molecular weight Mn of 2.000.000 g/mol). The specific surface area $A_{spec}$ of the membrane adsorber can be determined via BET measurments.

According to yet another preferred embodiment of the present invention, the concentration c(z, t) is calculated based on a general rate model, according to which $$Z = -v\frac{\partial c(z,t)}{\partial z} + D_{ax}\frac{\partial^2 c(z,t)}{\partial z^2} - \frac{(1-\varepsilon_b)}{\varepsilon_b} \cdot A \cdot k_{ext} \cdot (c(z,t) - c_f(z,r,t))$$

where $k_{ext}$ is the kinetic coefficient of the at least one compound regarding to film transfer, $c_f$ is the concentration of the at least one compound in a pore or an adsorptive layer of the stationary phase and r is the radius of the stationary phase particles, which can be determined by scanning electron microscopy.

If the stationary phase porosity $\varepsilon_{sp}$ has a nonzero value, the following equation needs to be considered in the general rate model.

$$\varepsilon_{sp}\frac{\partial c_p(z,r,t)}{\partial t} = \varepsilon_{sp}\frac{D_{eff}}{r^2}\frac{\partial}{\partial r}\left(r^2\frac{\partial c_p(z,r,t)}{\partial r}\right) - (1-\varepsilon_{sp})\frac{\partial q(z,r,t)}{\partial t}$$

where $D_{eff}$ is the effective diffusion coefficient.

In addition to the above methods for determining mass transfer parameters such as $k_{eff}$, $D_{eff}$ etc., further methods are available for a direct or indirect assessment. This includes but is not limited to an evaluation of signals resulting from different chromatographic experiments (as described in E. C. Ladd, T. Hahn, J. Seiler, S. A. Oelmeier, I. Asen, C. Silberer, L. Villain, J. Hubbuch, Modeling and simulation of anion-exchange membrane chromatography for purification of Sf9 insect cell-derived virus-like particles, J. Chromatogr. A. 1429 (2016) 142-154), tracer signal evaluation or batch uptake experiments.

In numerous cases, a chromatography device does not only contain the stationary phase/chromatography bed. Ancillary elements, like valves, tubings, flow distributors, etc. may be present. These ancillary elements, i.e. parts of the chromatography device through which the mobile phase flows and which are different from the chromatography bed are referred to as "external system". The influences of these ancillary elements on the hydrodynamic properties of the chromatography device can be taken account of as described in the following.

According to a preferred embodiment of the present invention, in step (iii), the chromatography device can be treated as a combination of a hypothetical stirred tank (ST), a hypothetical distributed plug flow pipe (DPF or PFP) and the chromatography bed, wherein the DPF is arranged downstream of the ST and the chromatography bed is arranged downstream of the DPF, as displayed in FIG. 17. (Alternatively, the chromatography device can be treated as a combination of only one of a hypothetical stirred tank (ST) and a hypothetical distributed plug flow pipe (DPF or PFP) with the chromatography bed.) Thus, the external system is preferably treated as a series of an ST and a DPF (external system "ST+DPF"). That is, according to a preferred embodiment of the present invention, c(z, t) is calculated based on the following equations:

$$\frac{\partial c_{out}^{ST}}{\partial t} = \frac{F}{V_{ST}}\left(c_{in}^{ST} - c_{out}^{ST}\right)$$

$$\frac{\partial c^{DPF}(z^{DPF},t)}{\partial t} = -v\frac{\partial c^{DPF}(z^{DPF},t)}{\partial z^{DPF}} + D_{ax}^{DPF}\frac{\partial^2 c^{DPF}(z^{DPF},t)}{\partial(z^{DPF})^2}$$

$$\frac{\partial c(z,t)}{\partial t} = -\frac{(1-\varepsilon_b)}{\varepsilon_b} \cdot \frac{\partial q(z,t)}{\partial t} - v\frac{\partial c(z,t)}{\partial z} + D_{ax}\frac{\partial^2 c(z,t)}{\partial z^2}$$

wherein $V_{SYS} + V_{ST} + V_{DPF}$ c(t=0,z)=0

$c_{out}^{ST} = c_{DPR}(z^{DPF}=0,t) = c_{in}^{DPF}(t)$ $c^{DPF}(z^{DPF}=z_{max}^{DPG},t) = c_{out}^{DPG}=(z=0,t)$ In the above equations, $z^{DPF}$ is the location in the (hypothetical) DPF, $z_{max}^{DPF}$ is the maximum value that $z^{DPF}$ can take (outlet of the DPF), z is the location in the chromatography bed, $c_{in}^{ST}$ is the concentration of the at least one compound at the inlet of the (hypothetical) ST, $c_{out}^{ST}$ is the concentration of the at least one compound at the outlet of the ST, $V_{ST}$ is the volume of the ST, F is the volumetric flow rate of the mobile phase through the ST, $C^{DPF}$ is the concentration of the at least one compound in the DPF, $c_{in}^{DPG}$ is the concentration of the at least one compound at the inlet of the DPF, $c_{out}^{DPG}$ is the concentration of the at least one compound at the outlet of the DPF, c(z=0, t) is the concentration of the at least one compound at the inlet of the chromatography bed, $D_{ax}^{DPG}$ is the axial dispersion coefficient of the DPF, which can be determined in a similar manner as the dispersion coefficient of the chromatography bed $D_{ax}$, $V_{SYS}$ is the total volume of the chromatography device which is accessible to the mobile phase except for the volume of the chromatography bed $V_b$, $V_{ST}$ is the volume of the stirred tank, and $V_{DPF}$ is the volume of the DPF. The further expressions are as defined above According to this preferred embodiment, the contribution of the external system is condensed in front of the column, meaning that the exit of the hypothetical stirred tank equals the inlet of the hypothetical DPF/PFP, and the exit of the DPF/PFP equals the inlet of the chromatography bed (see FIG. 17).

$V_{SYS}$ can be determined based on the geometry of the chromatographic apparatus. Specifically, $V_{SYS}$ can be determined in the absence of the chromatographic medium by applying an analysis of the first moment of a tracer signal.

$$V_{SYS} = F \mu_p$$

where F represents the volumetric flow rate and $\mu_p$ the first moment of a tracer peak, as already mentioned above. A regression of the complete concentration profile of a tracer substance leaving the system after a pulse injection leads to the complete parameter sets necessary to describe the fluid dynamic behavior of the external system. If a combination of ST and DPF is used to describe the behavior, an error minimization fitting procedure leads to $D_{ax}^{DPF}$, $V_{ST}$ and $V_{DPF}$.

As noted above, the calculation of c(z, t) in step (iii) may be based on partial differential equations (PDE, depending on time and space). To solve these equations, the PDEs can be transformed into ordinary differential equations (ODE). This is commonly done by describing the space dependency by a numerical method. One PDE is then transformed into n ODEs, where n is the degree of discretization. The numerical method used can be (but is not limited to) a finite difference method, orthogonal collocation or orthogonal collocation on finite elements.

In most cases, the resulting system of n ODEs cannot be solved analytically. A state of the art approach is the numerical integration at discrete time steps. Various different integration methods exist and can be used depending on the requirements. These are, but not limited to, implicit Euler method, explicit Euler method, variable step implicit Euler method and Runge-Kutta method.

Various commercial software bundles offer the possibility to solve the above PDE systems on which the calculation of c(z, t) in step (iii) may be based. These include Aspen Custom Modeler®, MatLab®, ChromX®, CADET®, GE PROMPS®.

In a further aspect, the present invention relates to a method of obtaining at least one chromatography method parameter, selected from the group consisting of stationary phase, mobile phase and chromatography device, comprising the steps of (I) executing the method of determining the concentration of at least one compound in a chromatography method of the present invention for n times, wherein n is an integer of 2 or more, wherein the n executions differ from one another with respect to at least one of the steps (ib) to (ie); and (II) selecting at least one stationary phase, at least one mobile phase, and/or at least one chromatography device based on the result of step (I).

Step (II) can be carried out by a human operator. Alternatively, step (II) can be automated, for instance by using a computer.

The complete description of a chromatographic process (e.g. a separation problem) by a mechanistic model is very beneficial with respect to parameter optimization and scale-up. The process window, which can be predicted, is directly correlated to the de-termined parameter space. Without the need for time and material consuming experimental effort on the pilot scale, optimized process parameters regarding the production scale can be directly predicted. Additionally, by using optimized process parameter sets, the overall process efficiency can be improved. With respect to the approach disclosed herein, the experimental effort for parameter determination on the lab scale is also significantly reduced. Based on a characterization of the chromatographic medium used, the validity of the disclosed approach can be confirmed and executed.

According to a preferred embodiment of the present invention, step (I) is carried out such that in each of the n executions, at least two different compounds are selected in step (ia) and in each of the n executions the at least two different compounds are the same. By this preferred embodiment, it is possible to find, among a set of chromatography method parameters, the best parameters for separating several compounds from one another.

In a further aspect, the present invention relates to a chromatography method comprising the above method of determining the concentration of at least one compound in a chromatography method, and (iv) a step of carrying out the chromatography.

By using the above method, the concentration c(z,t) can be reliably predicted so that the chromatography method can be controlled or adapted in accordance with the result for c(z,t) obtained in step (iii).

According to a preferred embodiment of the present invention, step (iii) includes calculating the concentration of the compound in the mobile phase at the outlet of the chromatography device $c_{out}(t)$ at several points in time t and step (iv) includes collecting the mobile phase at a time t where $c_{out}(t) > 0.0$ mmol/L, preferably where $c_{out}(t) > 0.00$ mmol/L. According to the present invention, the breakthrough curve of the at least one compound can be calculated in step (iii) and the mobile phase can be collected in accordance with the calculated breakthrough curve. It is particularly preferred that the mobile phase is collected at a time t where $c_{out}(t)$ is a significant concentration, i.e. a concentration of at least 0.01 μmol/L, preferably at least 0.001 μmol/L, particularly preferably at least 0.0001 μmol/L.

In a further aspect, the present invention relates to a chromatography method comprising the above method of obtaining at least one chromatography method parameter, and (III) a step of carrying out the chromatography based on the at least one chromatography parameter selected in step (II).

The present invention provides a process for rapidly, accurately and reliably calculating the concentration of at least one compound in a chromatography method despite fluctuations of the stationary phase's spatial structure due to variations of the composition of the mobile phase and/or the chromatography temperature.

FIG. 1 shows schematically the reversible swelling behavior of a charged hydrogel layer depending on the salt concentration of the mobile phase.

FIG. 2 displays porosity values $\varepsilon(c_S)$ determined for a dextrane 2000 kDa molecule on a Sartobind® Q Nano module depending on the salt concentration $c_S$.

FIG. 3 shows the dependence of the accessible volume fraction depending on the tracer molecule size, here pullulane in 10 mM KPi buffer at pH 7, 10 mM NaCl (see Example 2), wherein the hydrodynamic radius $r_H$ of the respective compound was determined as described in S. Viel, D. Capitani, L. Mannina, A. Segre, Diffusion-ordered NMR spectroscopy: A versatile tool for the molecular weight determination of uncharged polysaccharides, Biomacromolecules. 4 (2003) 1843-1847. doi:10.1021/bm0342638.

FIG. 4 displays stationary phase porosity values $\varepsilon_{sp}$ determined for Fractogel EMD $SO_3^-$ (M) depending on the salt concentration and a corresponding fit to a Boltzmann function (see Example 2).

FIG. 5 displays bulk porosity values $\varepsilon_b$ determined for Fractogel EMD $SO_3^-$ (M) depending on the salt concentration and a corresponding fit to a Boltzmann function (see Example 2).

FIG. 8 shows a size exclusion chromatogram for a cell culture supernatant fraction eluted from Sartobind® S after equilibration of 8 hours of Example 3a.

FIG. 15 shows simulation results at high salt concentrations of Example 7.

FIG. 16 (a) shows equilibrium adsorption data including a Langmuir isotherm fit of Example 8.

FIG. 16 (b) shows the dependence of the equilibrium binding constant on the salt concentration of Example 8.

FIG. 16 (c) shows the dependence of the maximum adsorbent capacity on the salt concentration of Example 8.

FIG. 19 schematically shows a preferred embodiment of the present invention.

The present invention is further illustrated by means of the following non-limiting Examples.

EXAMPLES

Example 1: Determination of Porosity Data Depending on Process Conditions (Step (iib))

The determination of a reversible swelling behavior can be easily performed using inverse size exclusion chromatography (iSEC) while varying the desired process conditions. Here, a specific example is given.

The stationary phase was a Sartobind® S membrane adsorber. Being a membrane adsorber, Sartobind® S has no internal porosity ($\varepsilon_b=\varepsilon_T$). It shows a pronounced reversible swelling behavior originating from its charged hydrogel surface modification. The chromatography device was a 3 mL ($V_b$=3 mL) Sartobind® Nano with 8 mm bed height.

The dead volume $V_{Dead}$ of the chromatography apparatus was determined by using 5 µL injections 0.25 g/L dextran ($M_w$=2000 kDa, determined by size exclusion chromatography), determined by the RI detector without the chromatographic device with 0.319±0.03 mL. The peak maxima and the first momentum analysis, respectively, was used to determine the dead volume. The chromatography device had a dead volume of 1 mL.

For the iSEC experiments the used buffer was 10 mM potassium phosphate buffer (KPi) buffer at pH 7. The salt concentration (NaCl) was varied from 0.01 to 0.8 M. The membrane adsorber (MA) was equilibrated for 15 membrane volumes with the desired salt concentration before being loaded with 50 µL injections 0.5 g/L dextran 2000 kDa. The resulting peak response was recorded using an IR detector.

The porosity $\varepsilon$ was determined based on the following equation.

$$\varepsilon = \frac{V}{F/\mu_p}$$

Figure 1:
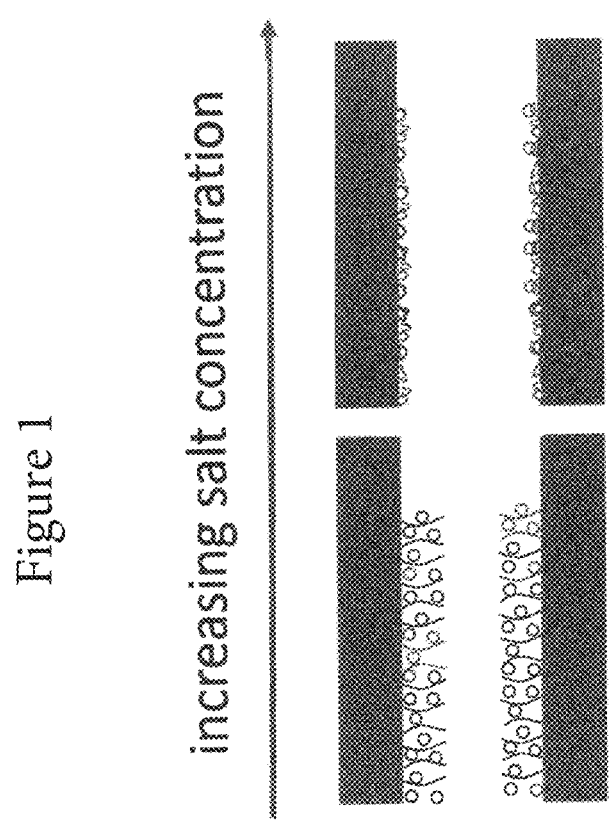
Figure 2:
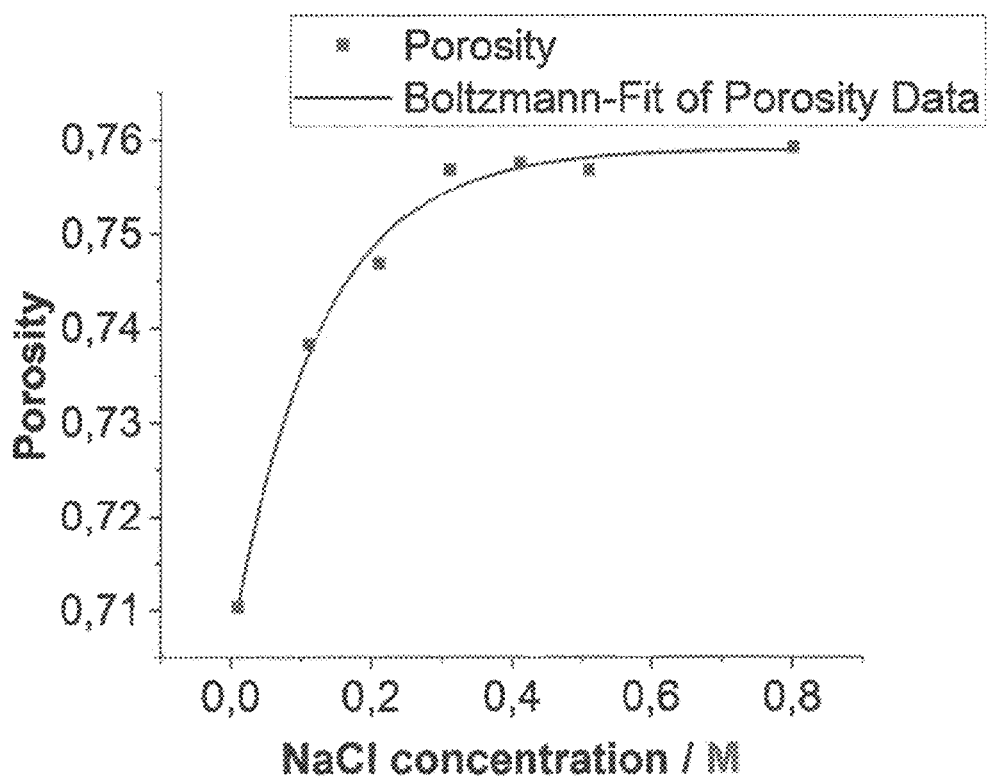

The obtained porosity values depending on the used salt concentration are shown in FIG. 2.

The data set was fitted using a Boltzmann function as shown in the following.

$$y = \frac{A_1 - A_2}{1 + e^{(x-x_0)/dx}} + A_2$$

The fit parameters were determined as follows:

| Parameter | Value |
|---|---|
| $A_1$ | −54.022 |
| $A_2$ | 0.759 |
| $x_0$ | −0.865 |
| dx | 0.125 |

Example 2: Determination of Porosity Data Depending on Process Conditions (Step (iib))

Figure 3:
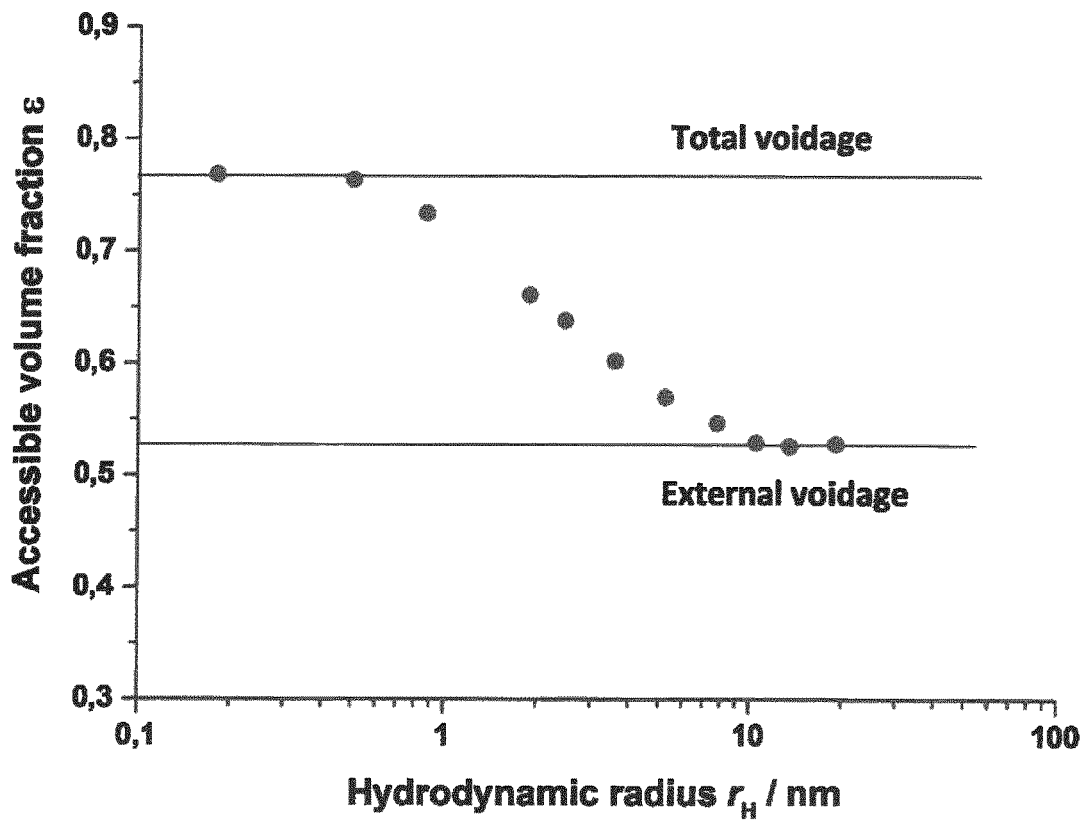

In the case of chromatographic media having an external and internal porosity, both values can be determined using reverse size exclusion chromatography as described above. Chromatographic media having an internal porosity show a different accessible volume fraction of the chromatographic bed depending on the tracer molecule size. An example for Fractogel EMD $SO_3^-$ (M) is shown in FIG. 3.

The stationary phase porosity $\varepsilon_{sp}$ can be calculated using the total porosity $\varepsilon_T$ and the external porosity $\varepsilon_b$ (voidage).

$$\varepsilon_{sp} = \frac{\varepsilon_T - \varepsilon_b}{1 - \varepsilon_b}$$

Figure 4:
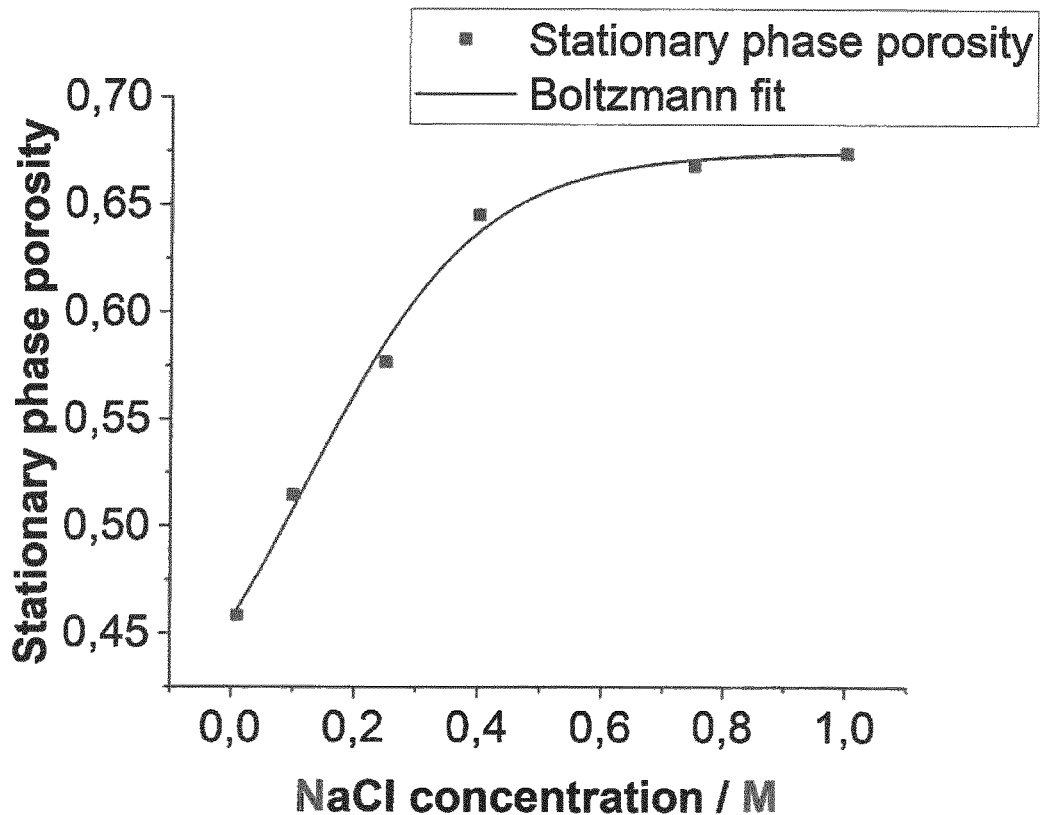
Figure 5:
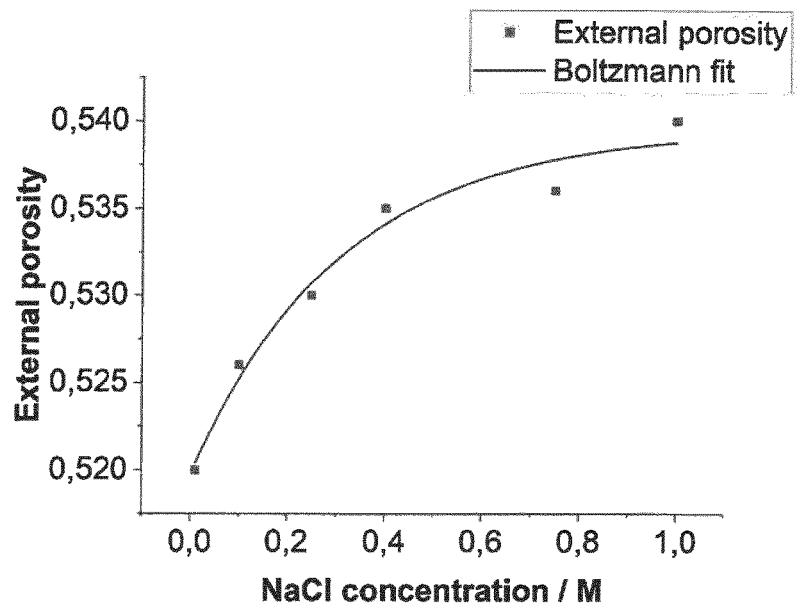

The total porosity $\varepsilon_T$ is accessible by a tracer molecule with complete accessibility of the internal porosity. In this example, acetone was used. A tracer molecule completely excluded can determine the bulk porosity $\varepsilon_b$. In this example, dextran having a molecular weight Mw of 2000 kDa was used. Using the above equation, the values obtained for $\varepsilon_T$ and $\varepsilon_b$ can be used to calculate the stationary phase porosity $\varepsilon_{sp}$ depending on the salt concentration. The obtained values for $\varepsilon_{sp}$ (stationary phase porosity) and $\varepsilon_b$ (external porosity) including Boltzmann fit and the corresponding parameters are shown in FIGS. 4 and 5.

Stationary phase porosity $\varepsilon_{sp}$:

| Parameter | Value |
| --- | --- |
| $A_1$ | 0.365 |
| $A_2$ | 0.674 |
| $x_0$ | 0.122 |
| dx | 0.140 |

Bulk porosity $\varepsilon_b$:

| Parameter | Value |
| --- | --- |
| $A_1$ | −72.89 |
| $A_2$ | 0.539 |
| $x_0$ | −2.548 |
| dx | 0.31 |

An excellent fit was obtained for both porosity values $\varepsilon_b$ and $\varepsilon_{sp}$ when using a Boltzmann function.

Example 3: Acquirinq Equilibrium Adsorption Data (step (iia))

In Example 3, equilibrium adsorption data for bovine serum albumin (BSA) on Sartobind® Q was obtained.

Figure 6:
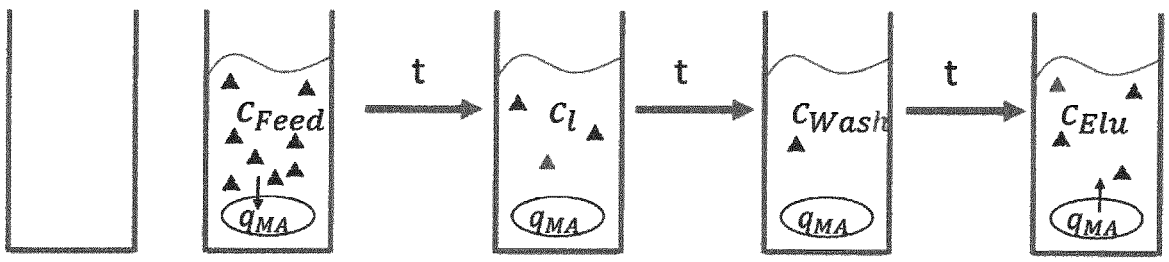
FIG. 6 shows the isotherm determination workflow of Example 3.

Determination of equilibrium adsorption data based on batch experiments as shown in Antibodies 2018, 7(1), 13; https://doi.org/10.3390/antib7010013, "Evaluation of Continuous Membrane Chromatography Concepts with an Enhanced Process Simulation Approach", Zobel, Stein, Strube, for Sartobind® Q, mean pore diameter of 3 µm and a ligand density of $$2\text{-}5 \frac{\mu eq}{cm^2},$$

was carried out with 0.1-5 g/L bovine serum albumin (BSA). The used buffer was 20 mM TRIS HCl buffer, at pH=7, with NaCl concentrations of 0 to 0.3 M NaCl. The pH-value was adjusted using HCl or NaOH. The round Sartobind® Q membrane adsorber (MA) sample with a diameter of 20 cm and a height of 0.024-0.028 cm was equilibrated 30 min in 20 mM TRIS HCl buffer with the respective pH and salt concentration. The volume of the buffer was 200 times the volume of the MA. After an equilibration time of 30 minutes, the MA was dabbed with paper and transferred in a 12 well plate cavity. The BSA was dissolved in TRIS HCl buffer corresponding to the experiment pH and salt concentration. The concentration of the BSA feed solution was measured by UVNis spectroscopy at 280 nm and added with 4 mL to the MA in the 12 well plate. After a residence time of at least 8 h the supernatant concentration was measured, the MA was again paper dabbed and transferred in a new well plate. Subsequently, the MA was eluted with 4 mL 20 mM TRIS HCl and 1 M NaCl for at least 4 h. The supernatant concentration was measured after the 4 h elution time. The foregoing process is schematically depicted in FIG. 6.

Figure 7:
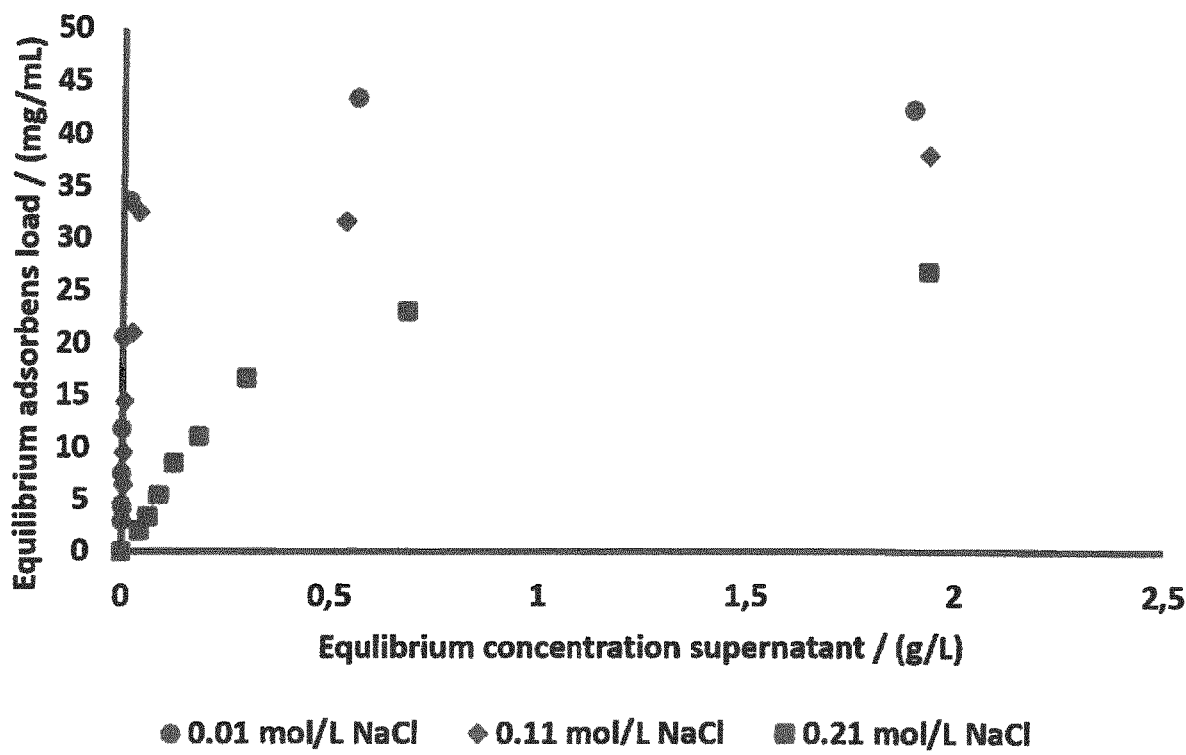
FIG. 7 shows equilibrium adsorption data for bovine serum albumin on Sartobind® Q of Example 3.

The obtained data sets for three different salt concentrations are shown in FIG. 7.

Example 3a: Acquiring Equilibrium Adsorption Data for Several Compounds

The method of Example 3 is also viable for multicomponent analysis. A prominent example is the simultaneous determination of equilibrium adsorption data for monoclonal antibodies (mAb) as well as their aggregates and contaminants. The batch experiments can be carried out in the same way but the supernatant and the elution has to be analyzed in a way that allows distinguishing between all components (mAb monomer, aggregates and further contaminants). For example, this can be achieved by size exclusion chromatography.

Figure 8:
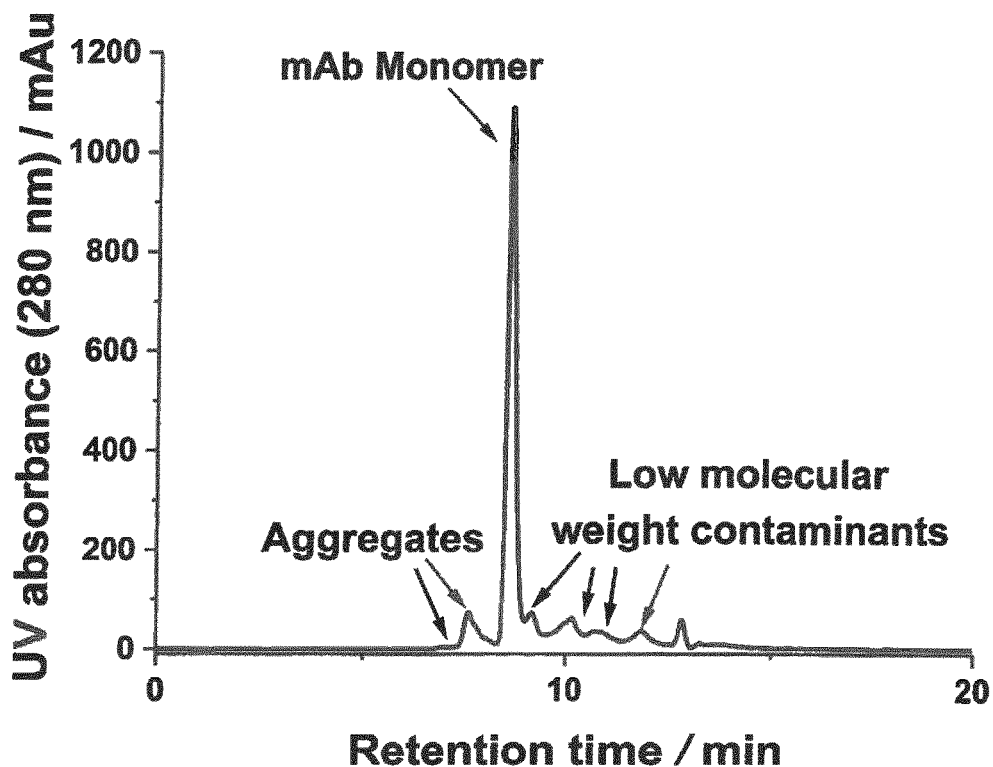
Figure 9:
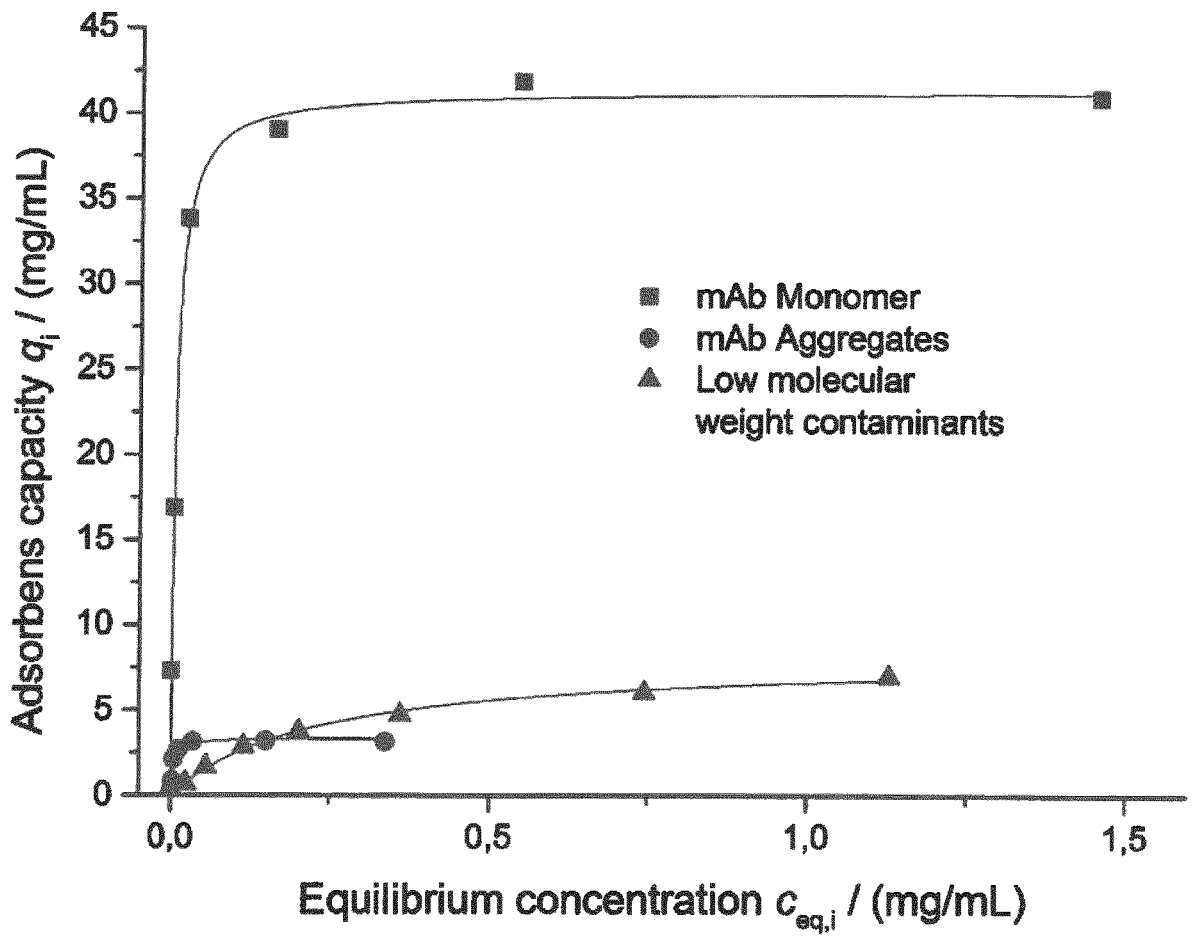
FIG. 9 shows equilibrium adsorption data for multiple components at a salt concentration of 20 mM for a hydrogel grafted chromatographic medium (hydrogel grafted membrane adsorber Sartobind® S) of Example 3a. The graphs represent Langmuir isotherm fits.

The resulting peaks of the obtained size exclusion chromatogram (see FIG. 8 for this Example) can be evaluated using a proper calibration to determine the concentration of the target components during the batch experiments as shown in FIG. 6. This leads to equilibrium adsorption data. An example is shown in FIG. 9 for a given salt concentration.

Figure 10:
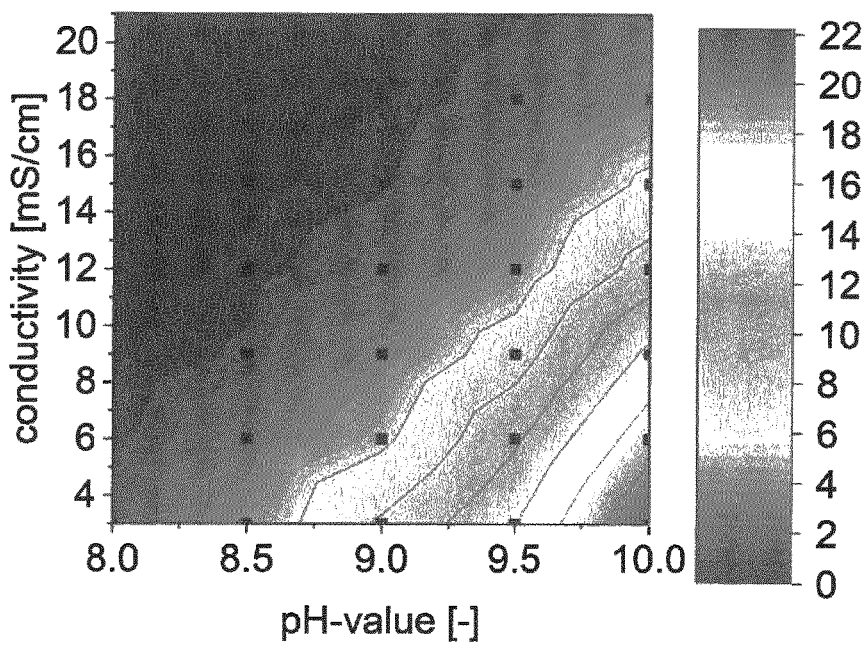
FIG. 10 shows an equilibrium adsorption data map for the monomer of a monoclonal antibody depending on conductivity and pH of Example 3b.
Figure 11:
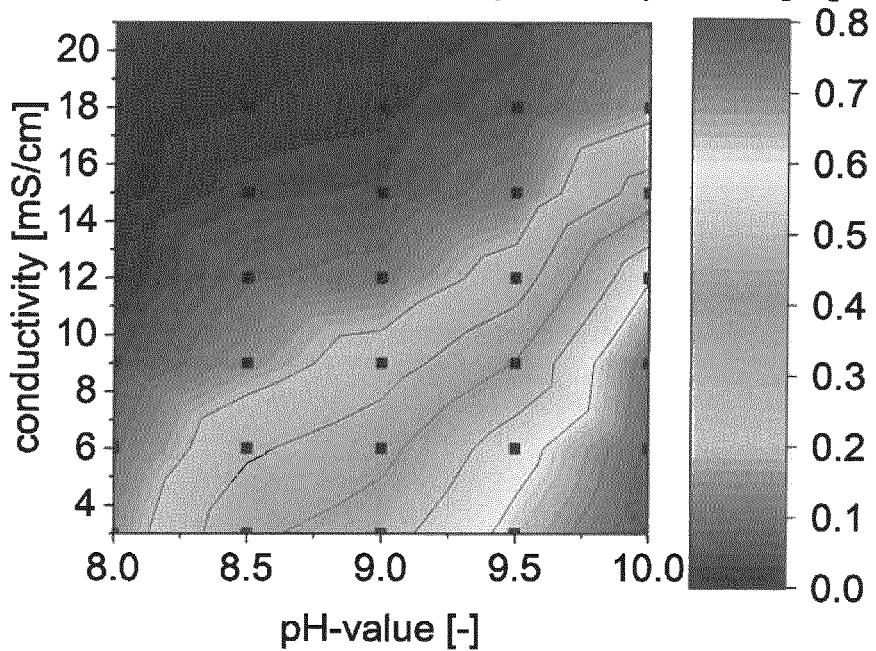
FIG. 11 shows an equilibrium adsorption data map for a dimer of a monoclonal antibody depending on conductivity and pH of Example 3b.

Example 3b: Acquiring Equilibrium Adsorption Data for Varying Salt Concentrations and Varying pH In the above Example 3, only the salt concentration was varied. Following the same approach, other influencing factors like the pH can also be varied, resulting in multidimensional adsorption data maps. FIGS. 10 and 11 show equilibrium adsorption data for the monoclonal antibody IgG and its dimer on Sartobind® Q depending on pH and salt concentration.

Example 4: Fitting of Data Sets to an SMA Isotherm (step (iia))

The data sets obtained in Example 3 were used to calculate protein characteristic charge $v_1$ and equilibrium constant k, furthermore the steric factor $\sigma_i$ was fitted using a computer-assisted least square regression at the three different salt concentrations ($C_S$=0.05, 0.15, 0.25 M) to an SMA adsorption isotherm to obtain the necessary adsorption model parameters in the investigated salt concentration area. The ionic capacity $\Lambda$ was 0.97 mol/L (Sartobind® Q).

$$c_i = \frac{q_i}{k} \cdot \left( \frac{c_1}{\Lambda - \sum_{i=2}^{n+1}(v_i + \sigma_i)q_i} \right)^{v_i}$$

Adsorption constant: k=7.55
Steric factor: $\sigma_i$=46.04
Characteristic charge: $v_i$=2.72
Salt concentration: $c_1$=0.05 M Example 5: Determining the Fluid Dynamic Behavior and Axial Dispersion Coefficient An Äkta™ Explorer from GE Healthcare was selected as the chromatography device (step (id)).

Figure 12:
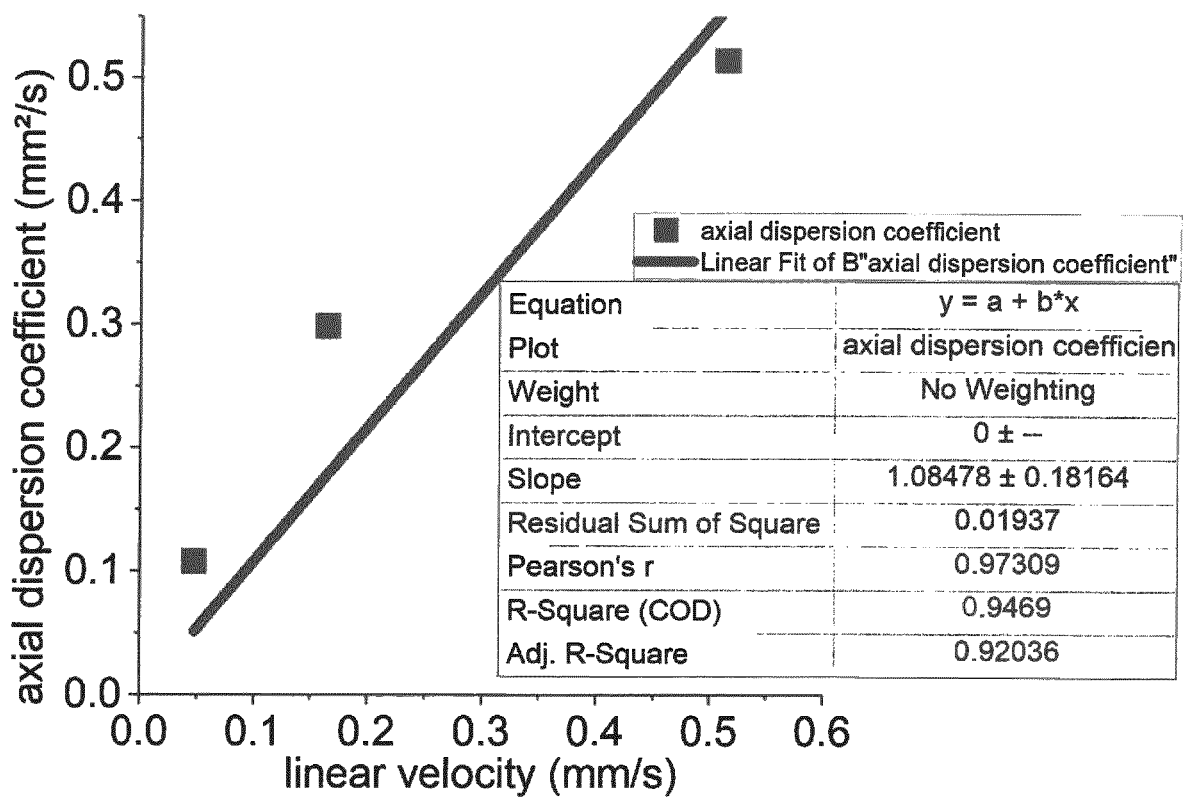
FIG. 12 shows the axial dispersion coefficient for the chromatographic medium depending on the linear flow velocity of Example 5.
Figure 13:
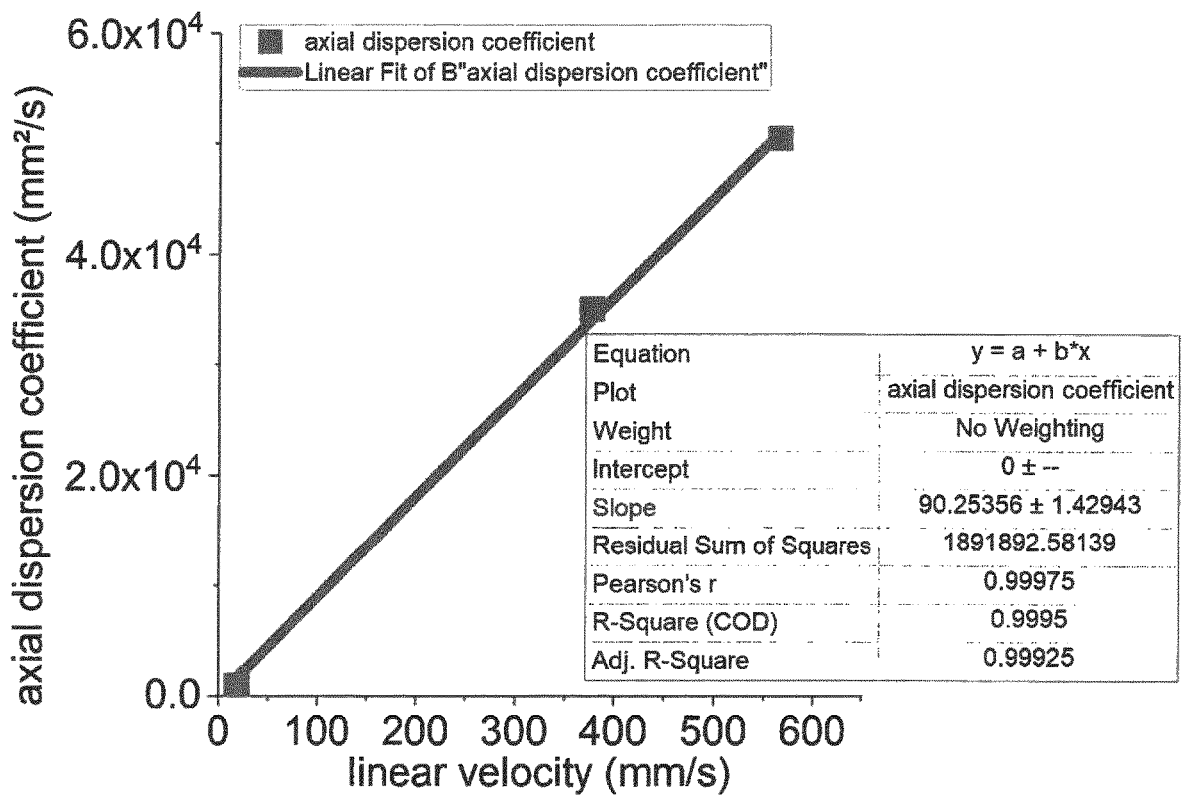
FIG. 13 shows the axial dispersion coefficient $D_{ax}^{DPG}$ of the DPF of the external system "ST+DPF" (see FIG. 17) depending on the linear flow velocity of Example 5.

The parameters $V_{SYS}$, $V_{ST}$, $V_{DPF}$ and $D_{ax}^{DPF}$ were determined as follows. Pulse injections of acetone (2 vol % in reverse-osmosis-water) or mAb (4 mg/mL in potassium phosphate (KPi) buffer, 10 mM, 20 mM NaCl, pH=6) were carried out in the absence of the chromatographic medium. The experiments were performed using different volumetric flow rates and buffer conditions. The resulting peak signals were evaluated following the method of moments and regressed using a least squares fitting procedure to obtain the desired values. The results of this procedure are given in FIGS. 12 and 13.

Example 6: Determination of Kinetic and Diffusion Coefficients

In accordance with the lumped pore model, the effective film-diffusion coefficient $D_{eff}$ was determined using mathematical correlations for a hydrogel modified membrane adsorber Sartobind® S:

The bulk diffusion coefficient was calculated using the Einstein-Stokes equation. In particular, intravenous immunoglobulin (IVIG, human γ-Globulin, SeraCare; r=5.2 nm) was dissolved in an aqueous sodium phosphate buffer (20 mM, pH=7) having a viscosity η of 1.05 mPa s at a temperature of 298 K.

The porosity values were determined using inverse size exclusion chromatography (iSEC). Briefly, the chromatographic bed was equilibrated for 50 column volumes (CVs) of the desired buffer (sodium phosphate buffer (20 mM, pH=7)) before being loaded with injections (100 µL) of a solution containing pullulan molecules (2 mg/mL) with a narrow molecular weight distribution. The mean molecular weight, directly linked to the mean hydrodynamic radius of the applied pullulan samples, was varied for every injection covering a wide range (Mn=320-740,000 g/moL). The elution profile was recorded and analyzed by an RI detector.

The effective diffusion coefficients were calculated using the following correlations.

$$D_{eff} = \frac{D_{bulk}}{\tau}$$

$$\tau = \frac{(2 - \varepsilon_{sp})^2}{\varepsilon_{sp}^2}$$

The values of the internal porosity $\varepsilon_p$ were determined by iSEC as described above.

For a membrane adsorber the following values were calculated depending on the respective target compound NaCl, acetone, and the monoclonal antibody IgG:

|  | Molecular diffusion coefficient/ (m²/s) | $k_{eff, A}$/ (1/s) |
|---|---|---|
| NaCl | 1.99 · 10⁻⁹ | 56.63 |
| Acetone | 1.14 · 10⁻⁹ | 23.67 |
| Monoclonal antibody | 4.00 · 10⁻¹¹ | 5.47 |

Example 7: Prediction of a Protein Purification Process (step (iii))

Figure 17:
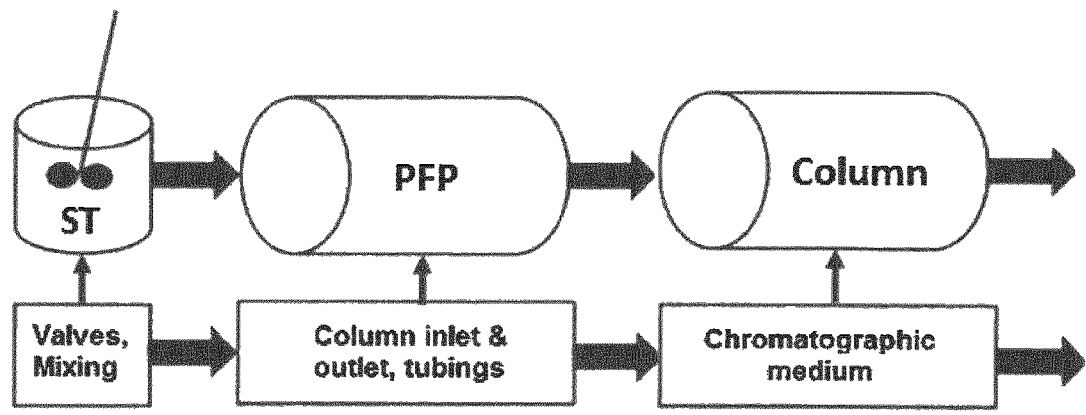
FIG. 17 shows a schematization of a chromatography device in accordance with a preferred embodiment of the present invention.
Figure 18:
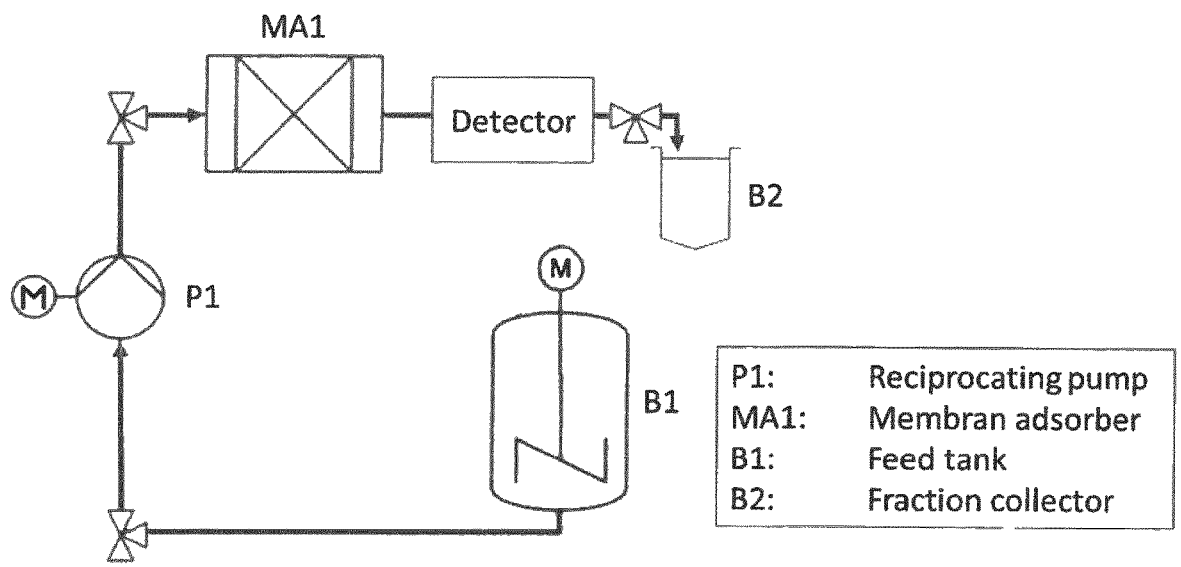
FIG. 18 shows an exemplary chromatography set-up.

The model parameter sets obtained in Examples 1 and 5 were used to predict the fluid-dynamic behavior of an acetone tracer pulse signal. The adsorption isotherm of acetone on the used membrane adsorber was found to be 0 (acetone does not bind to the stationary phase). The liquid chromatography (LC) system and membrane adsorber (MA) were simulated by the equilibrium dispersive model (EDM). Moreover, the chromatography apparatus was considered as a combination of an ST, DPF and the chromatography column, as described above and as shown in the following equations (see FIG. 17).

$$\frac{\partial c_{out}^{ST}}{\partial t} = \frac{F}{V_{ST}}\left(c_{in}^{ST} - c_{out}^{ST}\right)$$

Figure 14:
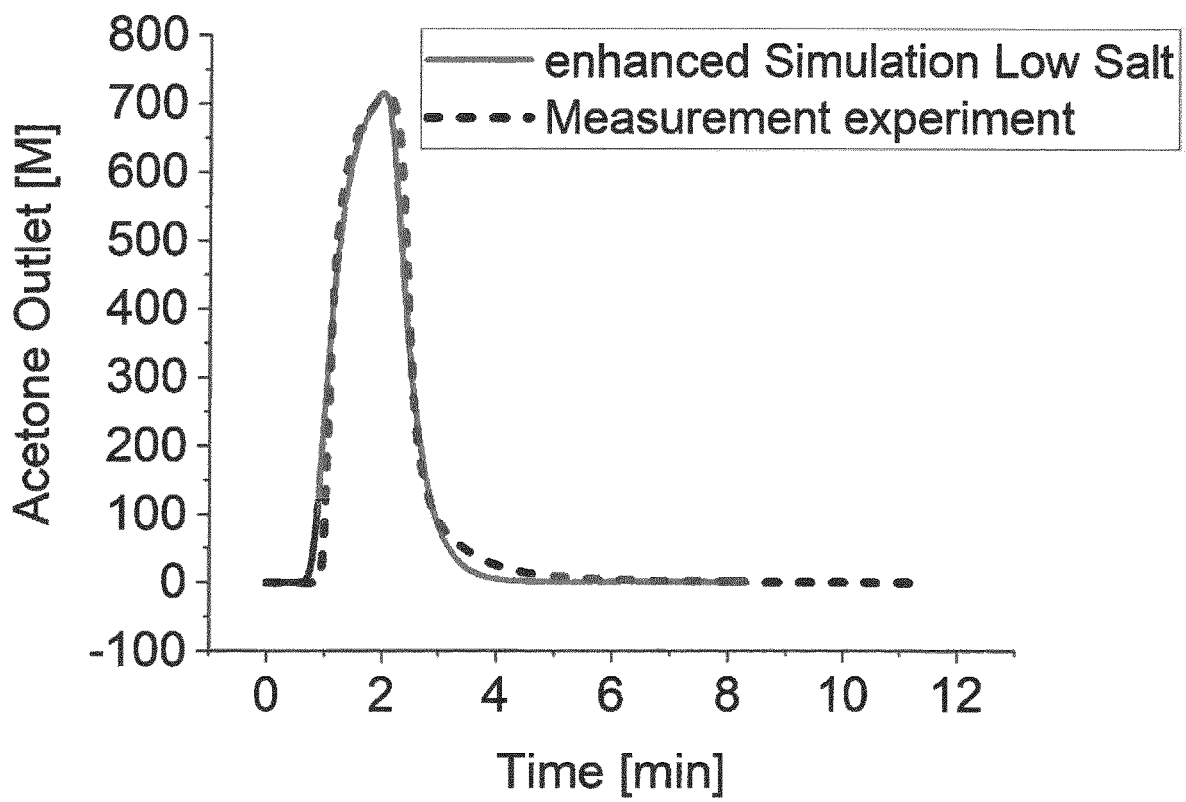
FIG. 14 shows simulation results at low salt concentrations of Example 7.

-continued $$\frac{\partial c^{DPF}(z^{DPF}, t)}{\partial t} = -v\frac{\partial c^{DPF}(z^{DPF}, t)}{\partial z^{DPF}} + D_{ax}^{DPF}\frac{\partial^2 c^{DPF}(z^{DPF}, t)}{\partial (z^{DPF})^2}$$

$$\frac{\partial c(z, t)}{\partial t} = -\frac{(1 - \varepsilon_b)}{\varepsilon_b} \cdot \frac{\partial q(z, t)}{\partial r} - v\frac{\partial c(z, t)}{\partial z} + D_{ax}\frac{\partial^2 c(z, t)}{\partial z^2}$$

wherein $V_{SYS} = V_{ST} + V_{DPF}$ $c(t = 0, z) = 0$ $c_{out}^{ST} = c^{DPF}(z^{DPF} = 0, t) = c_{in}^{DPF}(t)$ $c^{DPF}(z^{DPF} = z_{max}^{DPF}, t) = c_{out}^{DPF} = c(z = 0, t)$ Overall LC System had a pipe length of 2943 mm, a volume of 1.3 mL and a porosity of 1. The overall MA device is represented by 5.73 mm chromatography bed height, 3.5 mL chromatography bed volume and a porosity of 76-71% (0.76-0.71). The used MA was Sartobind® S in 10 mM KPi buffer at pH 7. Tracer experiments were carried out with a 2 mL injection volume of KPi buffer containing 5% acetone with 0 or 0.8 M additional sodium chloride at 4 mL/min. In FIG. 14, the low salt concentration simulation results and experimental data are compared. At low salt concentrations, conventional and improved model approach gave similar results. At high salt concentrations, the method according to the present invention yielded much better results than a method were the reversible swelling of the stationary phase was not taken into account (see FIG. 15). FIGS. 14 and 15 show the dramatic influence of a varying porosity value with respect to the fluid dynamic behavior.

The following table shows a comparison of a conventional simulation approach with the method according to the present invention corresponding to the half peak width FWHM (Full Width at Half Maximum) and the peak center. The inventive method gave a smaller deviation from the experimental value as the conventional approach.

|  | FWHM | Center |
|---|---|---|
| Deviation conventional simulation to experiment/% | 2.2 | 10.6 |
| Deviation inventive simulation to experiment/% | 2.0 | 2.6 |

Example 8: Fitting of Data Sets to a Langmuir Isotherm Step (iia))

A data set of equilibrium adsorption data obtained for IVIG on a hydrogel grafted chromatographic membrane was fitted to a Langmuir isotherm taking account of different NaCl concentrations. The results are shown in FIGS. 16(a) to 16(c).

As can be taken from FIG. 16(a), a Langmuir fit approximates the isotherm adsorption data with high accuracy.

The invention claimed is:

1. A method of determining the concentration of at least one compound in a chromatography method comprising the steps of
    selecting the at least one compound;
    selecting a stationary phase;
    selecting a mobile phase;
    selecting a chromatography device having a chromatography bed comprising the stationary phase and the mobile phase;
    selecting a chromatography temperature;

wherein at least one of the composition of the mobile phase and the chromatography temperature vary;

obtaining an adsorption isotherm of the at least one compound on the stationary phase for the varying composition of the mobile phase and/or the varying chromatography temperature;

determining at least the flow velocity of the mobile phase in the chromatography bed $v$ and the bulk porosity of the chromatography bed $\varepsilon_b$ for the varying composition of the mobile phase and/or the varying chromatography temperature; and calculating a concentration $c(z, t)$ of the at least one compound in the mobile phase at a predetermined location z of the chromatography device and at a predetermined time t based on the adsorption isotherm, the flow velocity $v$ and the bulk porosity $\varepsilon_b$.

2. The method according to claim 1, wherein the stationary phase is reversibly swellable.

3. The method according to claim 1, wherein in the determining step, the axial dispersion coefficient $D_{ax}$ of the at least one compound in the chromatography bed is further determined for the varying composition of the mobile phase and/or for the varying chromatography temperature and in the calculating step, the calculation of the concentration $c(z, t)$ is further based on the axial dispersion coefficient $D_{ax}$.

4. The method according to claim 1, wherein in the calculating step, $c(z, t)$ is calculated based on the following equation $$\frac{\partial c(z, t)}{\partial t} = Z$$

wherein Z is a sum including the following terms $$-\frac{(1 - \varepsilon_b)}{\varepsilon_b} \cdot \frac{\partial q(z, t)}{\partial t} \text{ and}$$

$$-v \frac{\partial c(z, t)}{\partial z}$$

wherein q (z, t) represents the binding capacity of the at least one compound by the stationary phase.

5. The method according to claim 4, wherein the sum Z further includes the term $$+D_{ax} \frac{\partial^2 c(z, t)}{\partial z^2}$$

6. The method according to claim 1, wherein the mobile phase is an aqueous medium.

7. The method according to claim 1, wherein a gel is formed on at least a part of the surface of the stationary phase when the mobile phase is contacted with the stationary phase.

8. The method according to claim 1, wherein at least a part of the surface of the stationary phase is constituted by a polymer that is bound to the surface of a stationary phase support structure.

9. The method according to claim 1, wherein the at least one compound comprises a protein and/or a drug.

10. A method of obtaining at least one chromatography method parameter, selected from the group consisting of stationary phase, mobile phase and chromatography device, comprising the steps of (I) executing the method according to claim 1 for n times, wherein n is an integer of 2 or more, wherein the n executions differ from one another with respect to at least one of the steps of selecting a stationary phase, selecting a mobile phase, and selecting a chromatography device; and (II) selecting at least one stationary phase, at least one mobile phase, and/or at least one chromatography device based on the result of step (I).

11. The method according to claim 10, wherein step (I) is carried out such that in each of the n executions, the selection of the at least one compound comprises selecting at least two different compounds and in each of the n executions the at least two different compounds are the same.

12. A chromatography method comprising:
the method of obtaining at least one chromatography method parameter according to claim 11, and further comprising:
(III) carrying out the chromatography based on the at least one chromatography parameter selected in step (II).

13. A chromatography method comprising:
the method of obtaining at least one chromatography method parameter according to claim 10, and further comprising:
(III) carrying out the chromatography based on the at least one chromatography parameter selected in step (II).

14. A chromatography method comprising:
the method of determining the concentration of at least one compound in a chromatography method according to claim 1, and further comprising:
carrying out the chromatography.

15. The chromatography method according to claim 14, wherein the calculating step includes calculating the concentration of the compound in the mobile phase at the outlet of the chromatography device $c_{out}(t)$ at several points in time t and the carrying out the chromatography step includes collecting the mobile phase at a time t where $c_{out}(t) > 0.0$ mmol/L.

* * * * *